(12) United States Patent
Lange

(10) Patent No.: US 7,689,833 B2
(45) Date of Patent: *Mar. 30, 2010

(54) METHOD AND APPARATUS FOR ELECTRO-BIOMETRIC IDENTITY RECOGNITION

(75) Inventor: Daniel H. Lange, Caesarea (IL)

(73) Assignee: IDesia Ltd., Caesarea (IL)

( * ) Notice: Subject to any disclaimer, the term of this patent is extended or adjusted under 35 U.S.C. 154(b) by 1401 days.

This patent is subject to a terminal disclaimer.

(21) Appl. No.: 10/984,200

(22) Filed: Nov. 9, 2004

(65) Prior Publication Data

US 2005/0281439 A1 Dec. 22, 2005

Related U.S. Application Data

(63) Continuation-in-part of application No. PCT/US03/23016, filed on Jul. 24, 2003.

(60) Provisional application No. 60/398,832, filed on Jul. 29, 2002.

(51) Int. Cl.
*G06F 21/00* (2006.01)
*G06F 7/04* (2006.01)
*G06F 17/30* (2006.01)
*H04L 29/06* (2006.01)
*H04L 9/32* (2006.01)
*G06K 9/00* (2006.01)

(52) U.S. Cl. ................ 713/186; 713/161; 713/168; 726/4; 726/5; 726/17; 726/18; 726/28; 726/29; 382/115

(58) Field of Classification Search ............. 713/186, 713/161, 168; 726/4, 5, 17, 18, 28, 29; 382/115
See application file for complete search history.

(56) References Cited

U.S. PATENT DOCUMENTS 4,685,465 A 8/1987 Klitgaard et al.

(Continued)

FOREIGN PATENT DOCUMENTS

EP 1 081 662 A2 3/2001

(Continued)

OTHER PUBLICATIONS

Biel, L., et al., 2001, "ECG Analysis: A New Approach in Human Identification," IEEE Transactions on Instrumentation and Measurement, vol. 50, No. 3, pp. 808-812.

(Continued)

*Primary Examiner*—Aravind K Moorthy
(74) *Attorney, Agent, or Firm*—Jones Day

(57) ABSTRACT

A method and apparatus for electro-biometric identity recognition or verification that produces and stores a first biometric signature that identifies a specific individual by forming the difference between a representation of the heartbeat pattern of the specific individual and a stored representation of common features of the heartbeat patterns of a plurality of individuals; after the producing step, the method and apparatus obtains a representation of the heartbeat pattern of a selected individual and produces a second biometric signature by forming the difference between the heartbeat pattern of the selected individual and the stored representation of common features of the heartbeat patterns of the plurality of individuals; it then compares the second biometric signature with the first biometric signature to determine whether the selected individual is the specific individual. The apparatus and method may be employed as a stand-alone unit or as part of another device pursuant to the many applications described herein.

48 Claims, 11 Drawing Sheets

U.S. PATENT DOCUMENTS

| | | | |
|---|---|---|---|
| 5,534,855 | A | 7/1996 | Shockley et al. |
| 5,719,950 | A | 2/1998 | Osten et al. |
| 5,892,824 | A | 4/1999 | Beatson et al. |
| 6,070,141 | A | 5/2000 | Houvener et al. |
| 6,231,346 | B1 | 5/2001 | Sagi-Dolev |
| 6,260,300 | B1 | 7/2001 | Klebes et al. |
| 6,293,904 | B1 | 9/2001 | Blazey et al. |
| 6,310,966 | B1 | 10/2001 | Dulude et al. |
| 6,335,688 | B1 | 1/2002 | Sweatte |
| 6,367,016 | B1 | 4/2002 | Lambert et al. |
| 6,483,929 | B1 | 11/2002 | Murakami et al. |
| 6,487,662 | B1 | 11/2002 | Kharon et al. |
| 6,490,680 | B1 | 12/2002 | Scheidt et al. |
| 6,633,090 | B2 | 10/2003 | Harter et al. |
| 2001/0016311 | A1 | 8/2001 | Sagi-Dolev |
| 2001/0031071 | A1 | 10/2001 | Nichols et al. |
| 2001/0031602 | A1 | 10/2001 | Sagi-Dolev |
| 2001/0035814 | A1 | 11/2001 | Uchida |
| 2002/0021601 | A1 | 2/2002 | Chornenky |
| 2002/0073306 | A1 | 6/2002 | Aluzzo et al. |
| 2002/0094111 | A1 | 7/2002 | Puchek et al. |
| 2002/0138768 | A1 | 9/2002 | Murakami et al. |
| 2002/0154036 | A1 | 10/2002 | Flick |
| 2002/0154793 | A1 | 10/2002 | Hillhouse et al. |
| 2002/0184500 | A1 | 12/2002 | Maritzen et al. |
| 2002/0193142 | A1 | 12/2002 | Stavenow et al. |
| 2003/0023855 | A1 | 1/2003 | Keogh et al. |
| 2003/0048000 | A1 | 3/2003 | Harter et al. |
| 2003/0098774 | A1 | 5/2003 | Chornenky |
| 2003/0098776 | A1 | 5/2003 | Friedli |
| 2003/0113001 | A1 | 6/2003 | Kato et al. |
| 2003/0115165 | A1 | 6/2003 | Hoya |
| 2003/0128867 | A1* | 7/2003 | Bennett ............... 382/115 |
| 2003/0135097 | A1 | 7/2003 | Wiederhold et al. |
| 2004/0010724 | A1 | 1/2004 | Brown et al. |
| 2004/0036574 | A1 | 2/2004 | Bostrom |
| 2004/0091138 | A1 | 5/2004 | Lee |
| 2004/0108377 | A1 | 6/2004 | Rietveld |
| 2004/0193068 | A1 | 9/2004 | Burton et al. |
| 2004/0193893 | A1* | 9/2004 | Braithwaite et al. ......... 713/186 |
| 2007/0003110 | A1 | 1/2007 | Gutta et al. |
| 2007/0016088 | A1* | 1/2007 | Grant et al. .............. 600/509 |
| 2008/0223926 | A1* | 9/2008 | Miller et al. ............... 235/382 |
| 2009/0119360 | A1* | 5/2009 | Robinson et al. ........... 709/203 |
| 2009/0132816 | A1* | 5/2009 | Lee ........................... 713/164 |
| 2009/0271496 | A1* | 10/2009 | Nakamura et al. ........... 709/217 |
| 2009/0287930 | A1* | 11/2009 | Nagaraja .................... 713/171 |

FOREIGN PATENT DOCUMENTS

| | | |
|---|---|---|
| EP | 1 120 757 A2 | 8/2001 |
| EP | 1 318 481 A1 | 6/2003 |
| EP | 1 415 683 A1 | 5/2004 |
| EP | 1 418 486 A2 | 5/2004 |
| WO | WO 84/04815 | 12/1984 |
| WO | WO 07/15032 | 4/1997 |
| WO | WO 98/13791 | 4/1998 |
| WO | WO 99/23614 | 5/1999 |
| WO | WO 00/46756 | 8/2000 |
| WO | WO 00/65292 | 11/2000 |
| WO | WO 00/70545 | 11/2000 |
| WO | WO 01/49369 A1 | 7/2001 |
| WO | WO 01/71642 A2 | 9/2001 |
| WO | WO 02/21763 A1 | 3/2002 |
| WO | WO 02/27686 A1 | 4/2002 |
| WO | WO 02/057998 A1 | 7/2002 |
| WO | WO 02/084602 A1 | 10/2002 |
| WO | WO 02/093330 A2 | 11/2002 |
| WO | WO 02/098054 A1 | 12/2002 |
| WO | WO 03/000015 A2 | 1/2003 |
| WO | WO 03/000015 A3 | 1/2003 |
| WO | WO 03/009113 A1 | 1/2003 |
| WO | WO 03/029048 A2 | 4/2003 |
| WO | WO 03/045740 A2 | 6/2003 |
| WO | WO 2004/010372 A1 | 1/2004 |
| WO | WO 2004/012388 A1 | 2/2004 |
| WO | WO 2004/048947 A1 | 6/2004 |
| WO | WO 2004/057546 A2 | 7/2004 |

OTHER PUBLICATIONS

Bolle, R.M., et al., "Guide to Biometrics," Springer-Verlag, 2003 (ISBN: 0-387-40089-3), pp. 8-10.

Mangona, A., et al., 2003, "Impact of age on QT interval and QT dispersion in healthy subjects: a regression analysis," Age and Ageing, vol. 32, pp. 326-331.

Kyoso M. et al, Development of an ECG identification system, Proceedings of the 23rd Annual International Conference of the IEEE Engineering in Medicine and Biology Society, vol. 1 (2001) 3721-3723.

Biel L. et al, ECG analysis: a new approach in human identification, Proceedings of the 16th IEEE Venice, Italy (1999), 557-561.

Tompkins, W.J., et al., "A Portable Microcomputer-Based System for Biomedical Applications," Biomedical Sciences Instrumentation, Apr. 17-18, 1978, pp. 61-66, vol. 14, RMBS-ISA, USA.

Chien, I.C., et al., "Computer Methods for Analysing the High-Frequency Electrocardiogram," Medical & Biological Engineering & Computing, May 1980, pp. 303-312, vol. 18, No. 3, International Federation for Medical & Biological Engineering, England.

Kim, Y., et al., "Forward and Inverse High-Frequency Electrocardiography," Medical & Biological Engineering & Computing, Jan. 1981, pp. 11-22, vol. 19, No. 1, International Federation for Medical & Biological Engineering, England.

Abenstein, J.P., et al., "A New Data-Reduction Algorithm for Real-Time ECG Analysis," IEEE Transactions on Biomedical Engineering, Jan. 1982, pp. 43-48, vol. BME-29, No. 1, IEEE Engineering in Medicine and Biology Society, University of Wisconsin, Madison, WI, USA.

Thakor, N.V., et al., "A Battery-Powered Digital Modem for Telephone Transmission of ECG Data," IEEE Transactions on Biomedical Engineering, May 1982, pp. 355-359, vol. BME-29, No. 5, IEEE Engineering in Medicine and Biology Society, University of Wisconsin, Madison, WI, USA.

Tompkins, W.J., "Trends in Ambulatory Electrocardiography," IEEE Transactions on Biomedical Engineering, Aug. 1982, p. 600, vol. BME-29, No. 8, IEEE Engineering in Medicine and Biology Society, University of Wisconsin, Madison, WI, USA.

Weisner, S.J., et al., "A Compact, Microprocessor-Based ECG ST-Segment Analyzer for the Operating Room," IEEE Transactions on Biomedical Engineering, Sep. 1982, pp. 642-649, vol. BME-29, No. 9, IEEE Engineering in Medicine and Biology Society, University of Wisconsin, Madison, WI, USA.

Sahakian, A.V., et al., "A Microprocessor-Based Arrhythmia Monitor/Recorder for the Operating and Recovery Rooms," Medical Instrumentation, Mar.-Apr. 1983, pp. 131-134, vol. 17, No. 2, University of Wisconsin, Madison, WI, USA.

Furno, G.S., et al., "A Learning Filter for Removing Noise Interference," IEEE Transactions on Biomedical Engineering, Apr. 1983, pp. 31-34, vol. BME-30, No. 4, IEEE Engineering in Medicine and Biology Society, University of Wisconsin, Madison, WI, USA.

Ge, J., et al., "High-Frequency ECG Feature Recognition Using a High Level Language," Biomedical Sciences Instrumentation, Apr. 18-19, 1983, pp. 31-34, vol. 19, RMBS-ISA, USA.

Thakor, N.V., et al., "Optimal QRS Detector," Medical & Biological Engineering & Computing, May 1983, pp. 343-350, vol. 21, No. 3, Int'l Federation for Medical & Biological Engineering, England.

Ahlstrom, M.L., et al., "Automated High-Speed Analysis of Holter Tapes with Microcomputers," IEEE Transactions on Biomedical Engineering, Oct. 1983, pp. 651-657, vol. BME-30, No. 10, IEEE Engineering in Medicine and Biology Society, University of Wisconsin, Madison, WI, USA.

Thakor, N.V., et al., "Design, Implementation and Evaluation of a Microcomputer-Based Portable Arrhythmia Monitor," Medical &

Biological Engineering & Computing, Mar. 1984, pp. 151-159, vol. 22, No. 2, Int'l Federation for Medical & Biological Engineering, England.

Thakor, N.V., et al., "Estimation of QRS Complex Power Spectra for Design of a QRS Filter," IEEE Transactions on Biomedical Engineering, Nov. 1984, pp. 702-706, vol. BME-31, No. 11, IEEE Engineering in Medicine and Biology Society, University of Wisconsin, Madison, WI, USA.

Pan, J., et al., "A Real-Time QRS Detection Algorithm," IEEE Transactions on Biomedical Engineering, Mar. 1985, pp. 230-236, vol. BME-32, No. 3, IEEE Engineering in Medicine and Biology Society, University of Wisconsin, Madison, WI, USA.

Ahlstrom, M.L., et al., "Digital Filters for Real-Time ECG Signal Processing Using Microprocessors," IEEE Transactions on Biomedical Engineering, Sep. 1985, pp. 708-713, vol. BME-32, No. 9, IEEE Engineering in Medicine and Biology Society, University of Wisconsin, Madison, WI, USA.

Ge, J.G., et al., "High-Frequency Electrocardiogram Analyzer," IEEE Transactions on Biomedical Engineering, Dec. 1986, pp. 1137-1140, vol. BME-33, No. 12, IEEE Engineering in Medicine and Biology Society, University of Wisconsin, Madison, WI, USA.

Hamilton, P.S., et al., "Quantitative Investigation of QRS Detection Rules Using the MIT/BIH Arrhythmia Database," IEEE Transactions on Biomedical Engineering, Dec. 1986, pp. 1157-1165, vol. BME-33, No. 12, IEEE Engineering in Medicine and Biology Society, University of Wisconsin, Madison, WI, USA.

Hamilton, P.S., et al., "Compression of the Ambulatory ECG by Average Beat Subtraction and Residual Differencing," IEEE Transactions on Biomedical Engineering, Mar. 1991, pp. 253-259, vol. 38, No. 3, Dept. of Electrical and Computer Engineering, University of Wisconsin, Madison, WI, USA.

Hamilton, P.S., et al., "Theoretical and Experimental Rate Distortion Performance in Compression of Ambulatory ECG's," IEEE Transactions on Biomedical Engineering, Mar. 1991, pp. 260-266, vol. 38, No. 3, Dept. of Electrical and Computer Engineering, University of Wisconsin, Madison, WI, USA.

Xue, Q., et al., "Neural-Network-Based Adaptive Matched Filtering for QRS Detection," IEEE Transactions on Biomedical Engineering, Apr. 1992, pp. 317-329, vol. 39, No. 4, Dept. of Electrical and Computer Engineering, University of Wisconsin, Madison, WI, USA.

Hu, Y.H., et al., "Applications of Artificial Neural Networks for ECG Signal Detection and Classification," Journal of Electrocardiology, 1993, pp. 66-73, vol. 26 Supplement, Churchill Livingstone, Madison, WI, USA.

Luo, S., et al., "Parameter Evaluation of the Inverse Power-Law Spectrum of Heart Rate. A Quantitative Approach for ECG Arrhythmia Analysis," Journal of Electrocardiology, 1994, pp. 46-52, vol. 27 Supplement, Churchill Livingstone, Madison, WI, USA.

Panescu, D., et al., "A Database of Cardiac Arrhythmias," Academic Emergency Medicine, Jan. 1995, pp. 46-49, vol. 2, No. 1, University of Wisconsin, Madison, WI, USA.

Afonso, V.X., et al., "Detecting Ventricular Fibrillation: Selecting the Appropriate Time-Frequency Analysis Tool for the Application," IEEE Engineering in Medicine & Biology, Mar./Apr. 1995, pp. 152-159, vol. 14, No. 2, USA.

Afonso, V.X., et al., "Comparing Stress ECG Enhancement Algorithms: With an Introduction to a Filter Bank Based Approach," IEEE Engineering in Medicine & Biology, May/Jun. 1996, pp. 37-44, vol. 15, No. 3, USA.

Hu, Y.H., et al., "A Patient-Adaptable ECG Beat Classifier Using a Mixture of Experts Approach," IEEE Transactions on Biomedical Engineering, Sep. 1997, pp. 891-900, vol. 44, No. 9, Dept. of Electrical and Computer Engineering, University of Wisconsin, Madison, WI, USA.

Afonso, V., et al., "Use of Filter Banks in ECG Processing," Biomedical Engineering—Applications, Basis & Communications, Oct. 25, 1997, pp. 297-302, vol. 9, No. 5, Dept. of Electrical & Computer Engineering, University of Wisconsin, Madison, WI, USA.

Afonso, Valtino X., et al., "ECG Beat Detection Using Filter Banks," IEEE Transactions on Biomedical Engineering, Feb. 1999, pp. 192-202, vol. 46, No. 2, Endocardial Solutions, Inc., Saint Paul, MN, USA.

Wieben, O., et al., "Classification of Premature Ventricular Complexes Using Filter Bank Features, Induction of Decision Trees and a Fuzzy Rule-Based System," Medical & Biological Engineering & Computing, Sep. 1999, pp. 560-565, vol. 37, No. 5, Dept. of Electrical & Computer Engineering, University of Wisconsin, Madison, WI, USA.

Kyoso, Masaki, et al., "Development of an ECG Identification System," Papers from 23rd Annual Int'l Conference of the IEEE Engineering in Medicine and Biology Society, Oct. 25-28, 2001, Dept. of Information and Computer Sciences, Kanagawa Inst. of Technology, Istanbul, Turkey.

Harland, C.J., et al., "Electric potential probes—new directions in the remote sensing of the human body," Meas. Sci. Technol. (2002) 163-169, vol. 13, IOP Publishing Ltd., UK.

Apr. 27, 2009 USPTO Office Action in child U.S. Appl. No. 11/270,807.

May 12, 2009 Amendment and Response to USPTO Office Action dated Apr. 27, 2009 in child U.S. Appl. No. 11/270,807.

* cited by examiner

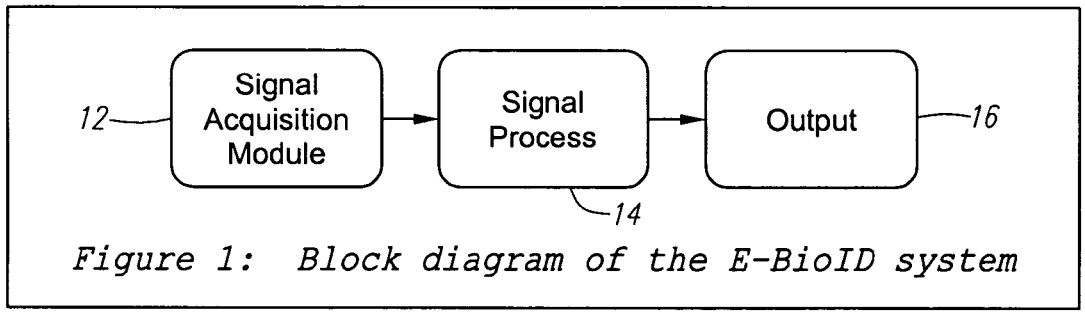
Figure 1: Block diagram of the E-BioID system
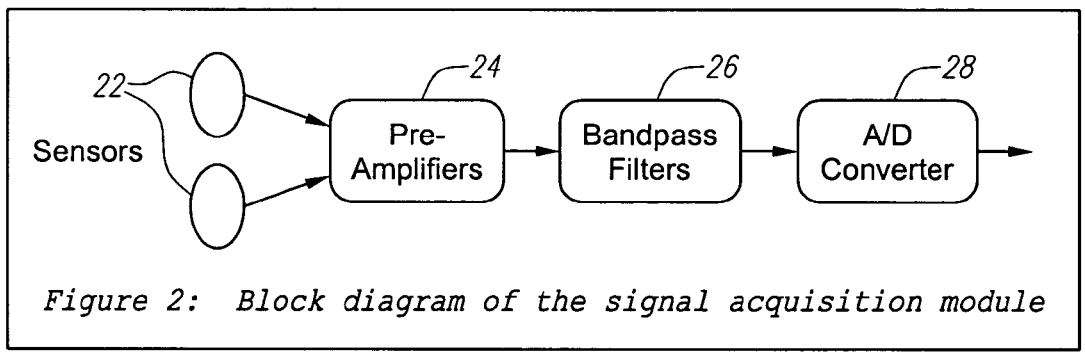
Figure 2: Block diagram of the signal acquisition module
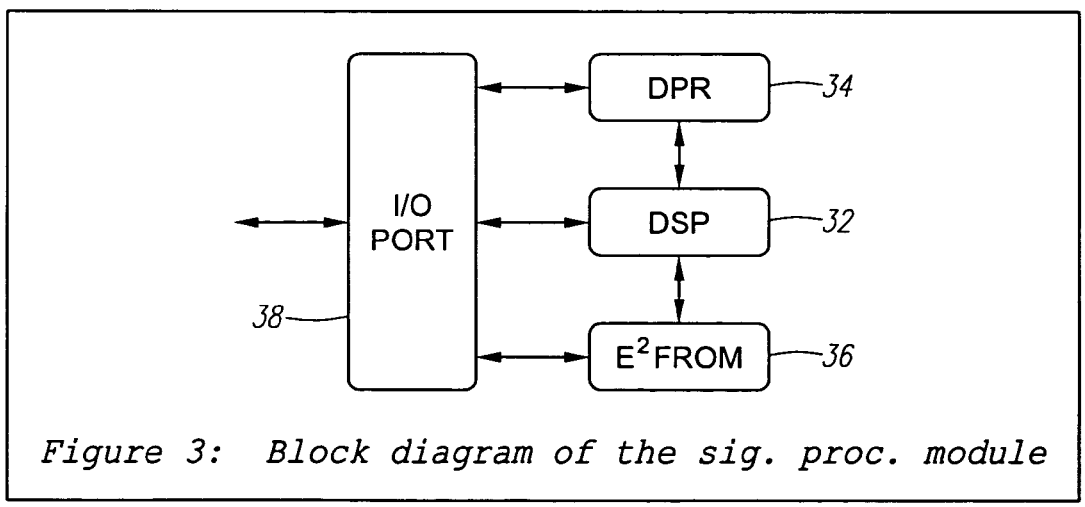
Figure 3: Block diagram of the sig. proc. module

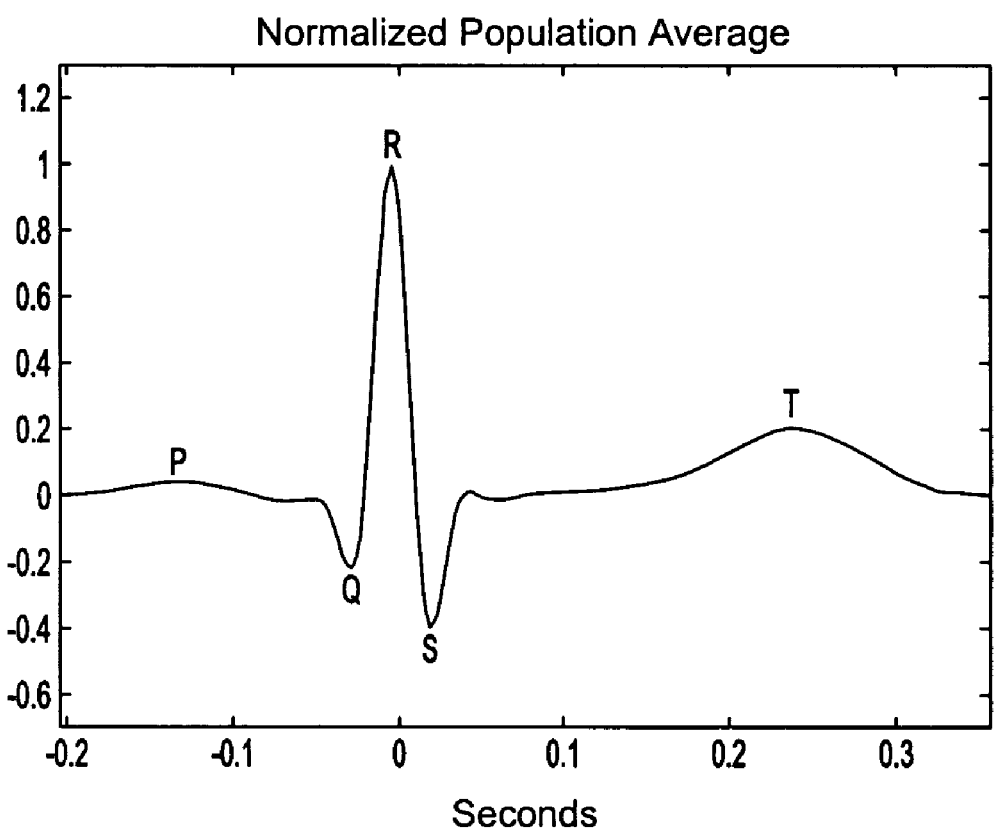
Figure 4: Normalized grand-average

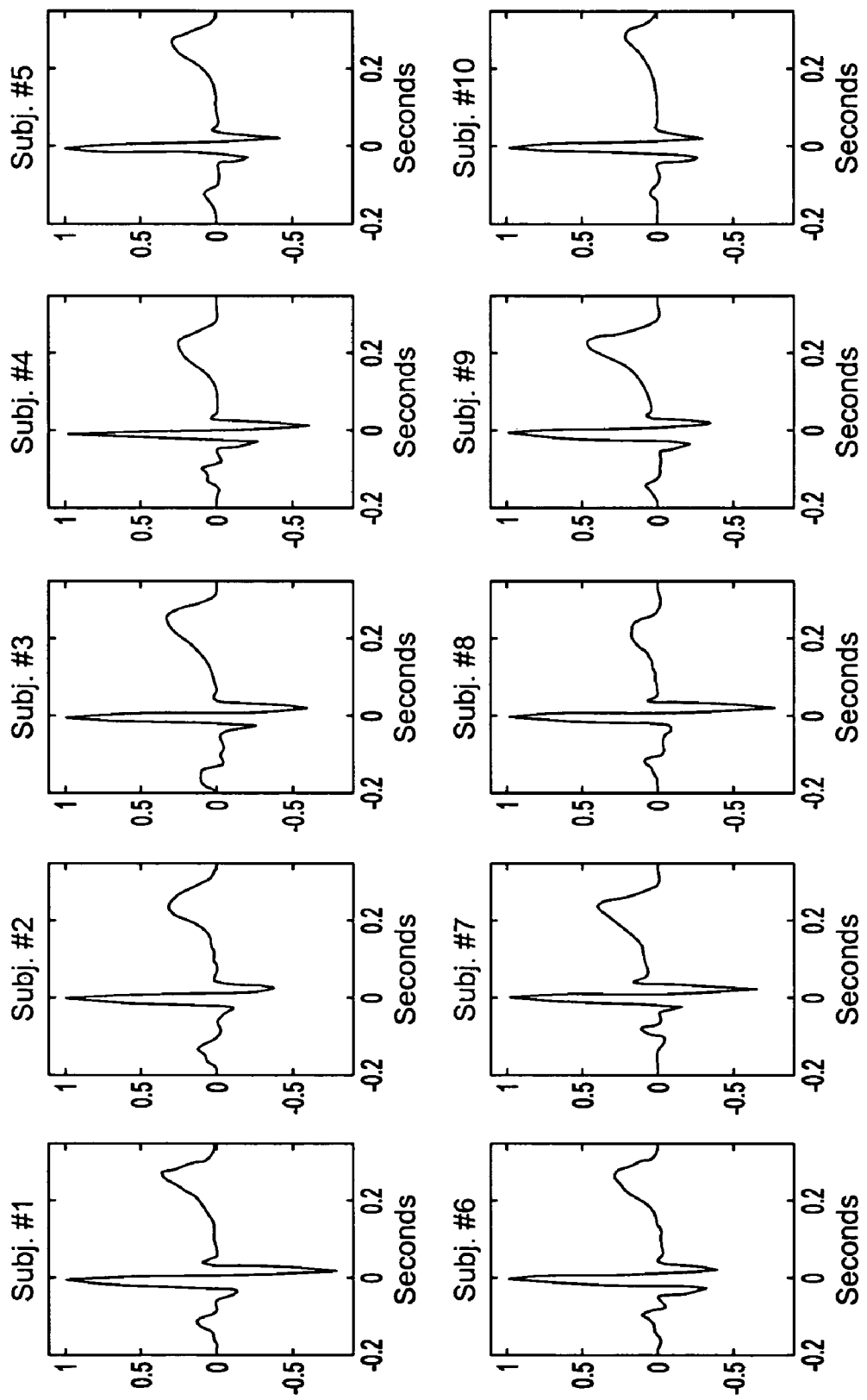
Figure 5: Electro-cardiologic signals of ten subjects

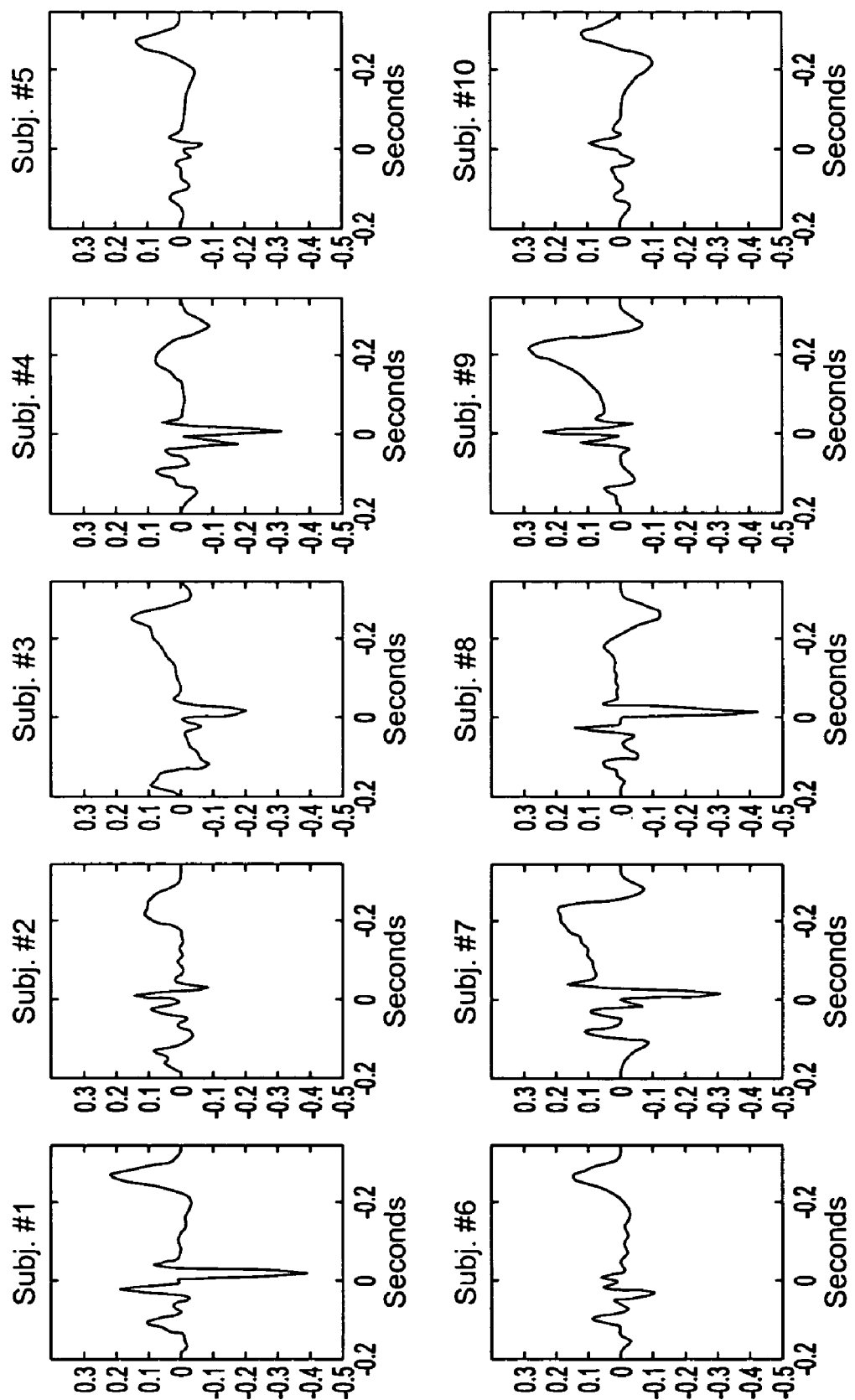
Figure 6: Signature templates of the above ten subjects

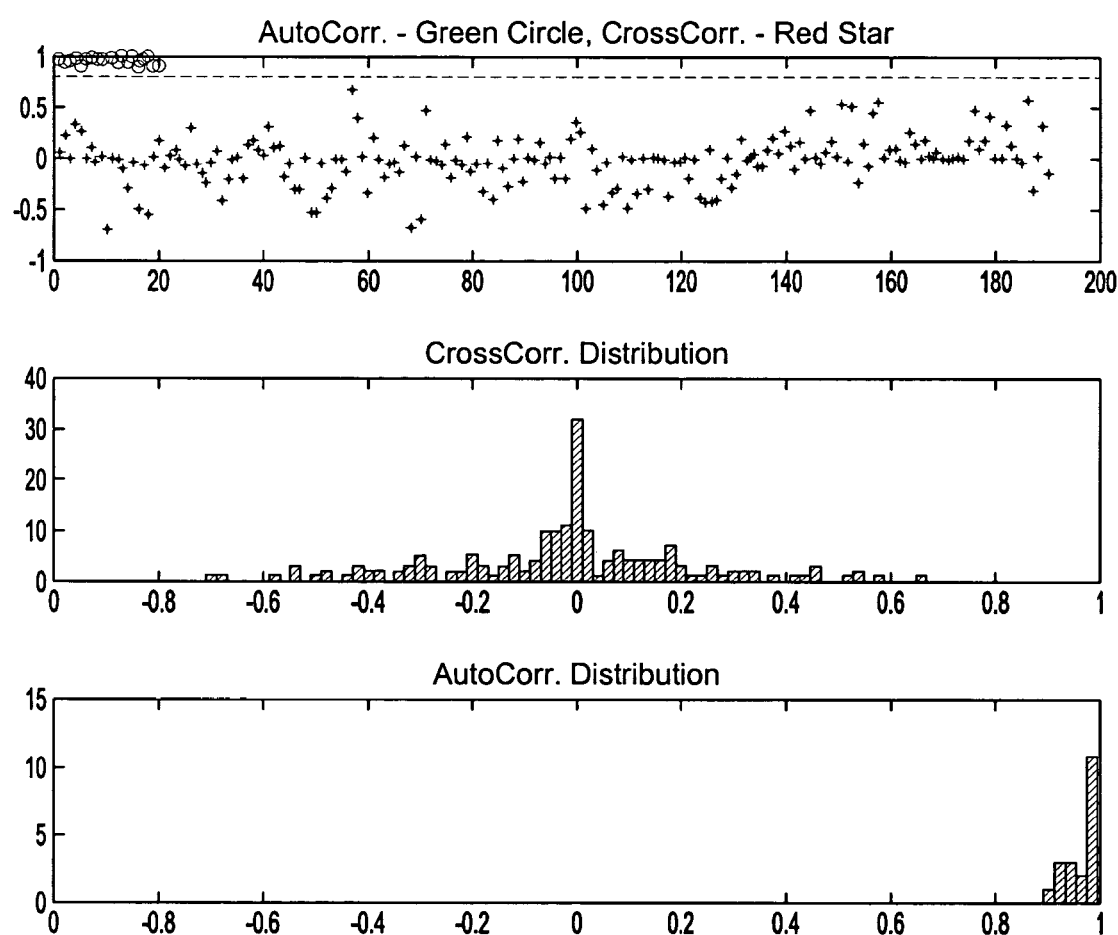
Figure 7: Distributions of correlation data

| 1-tailed limit | Unlikelihood | z score |
|---|---|---|
| 99.99% | 0.01% | 3.71 |
| 99.90% | 0.10% | 3.09 |
| 99.50% | 0.50% | 2.58 |
| 99.00% | 1.00% | 2.33 |
| 97.50% | 2.50% | 1.96 |
| 95.00% | 5.00% | 1.65 |
| 90.00% | 10.00% | 1.28 |
*Figure 8*
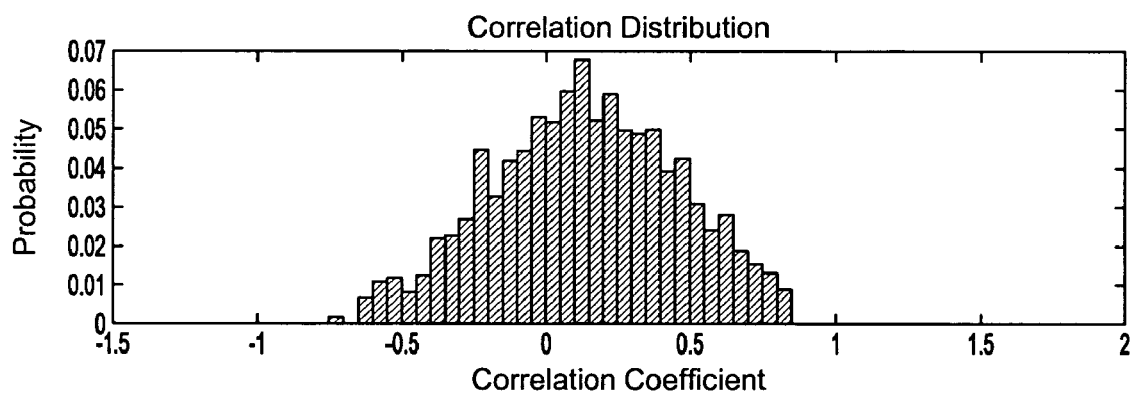
*Figure 9A*
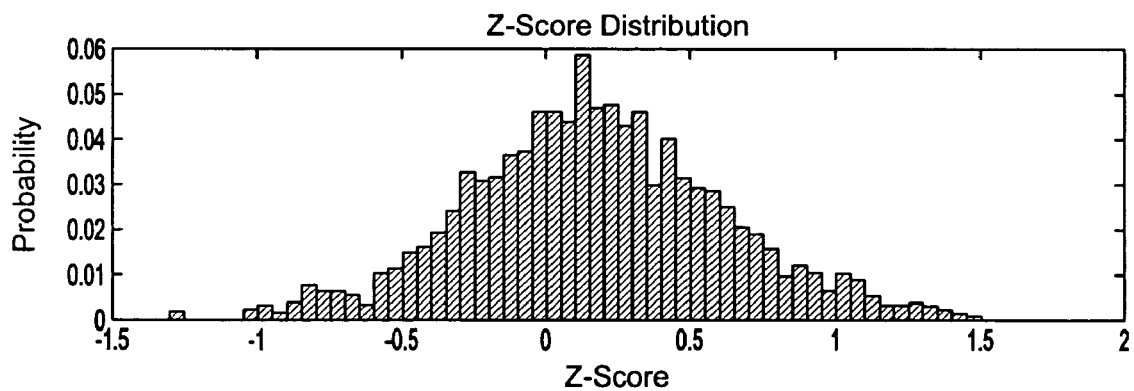
*Figure 9B*

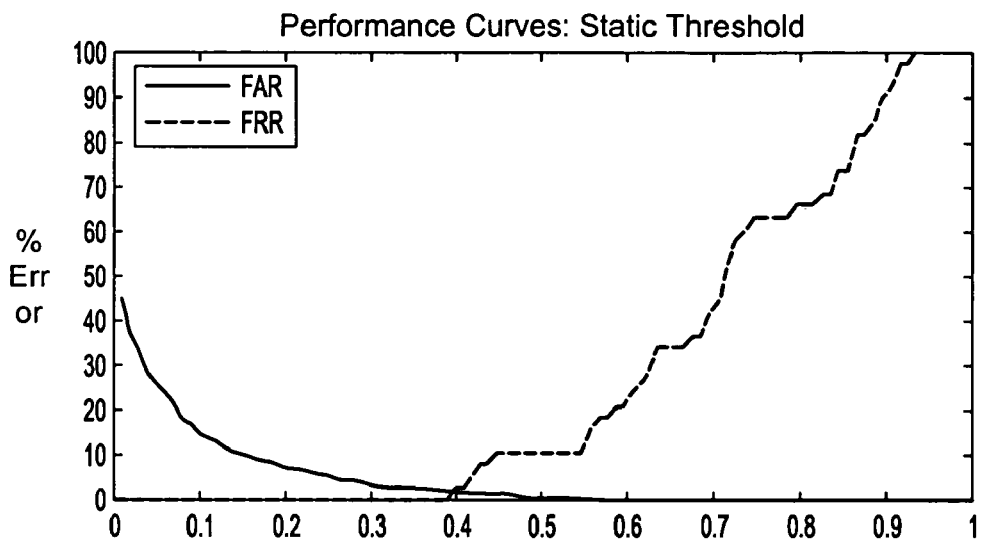
Figure 10: Identification Performance Curves (Static)
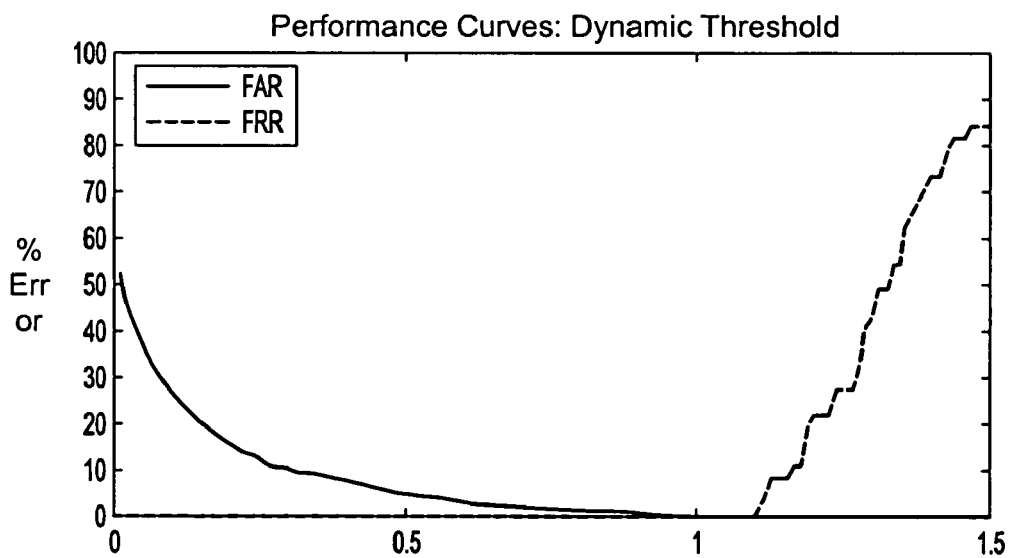
Figure 11: Identification Performance Curves (Dynamic)

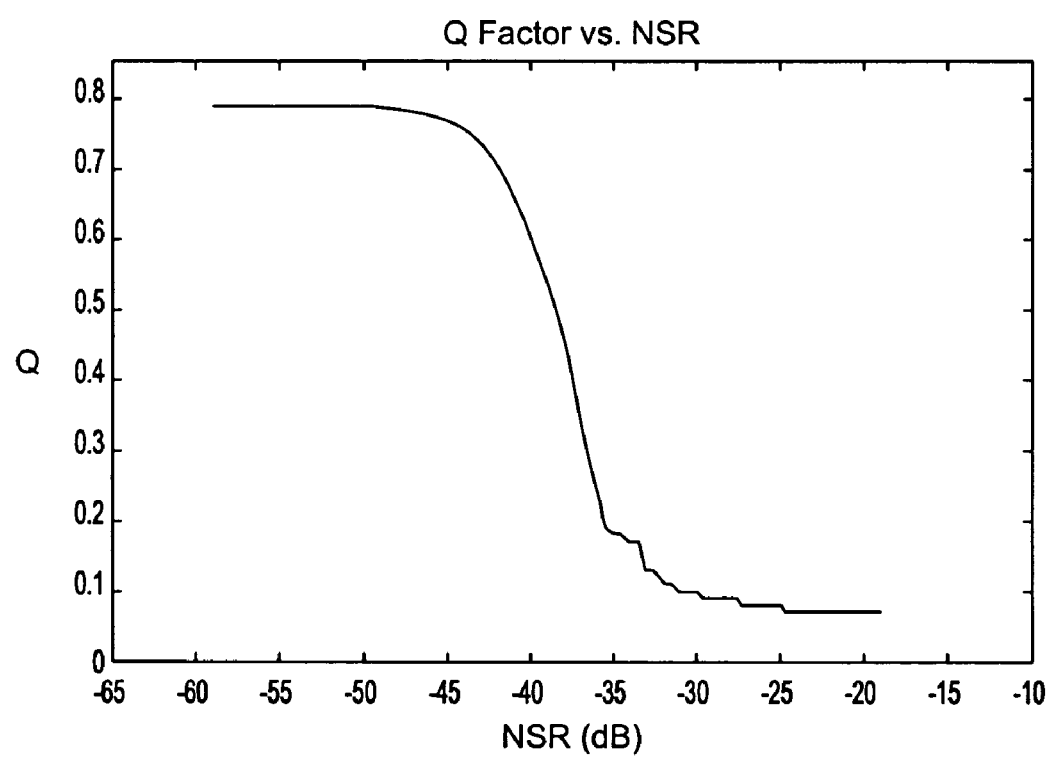
Figure 12: Signal Quality as a function of NSR

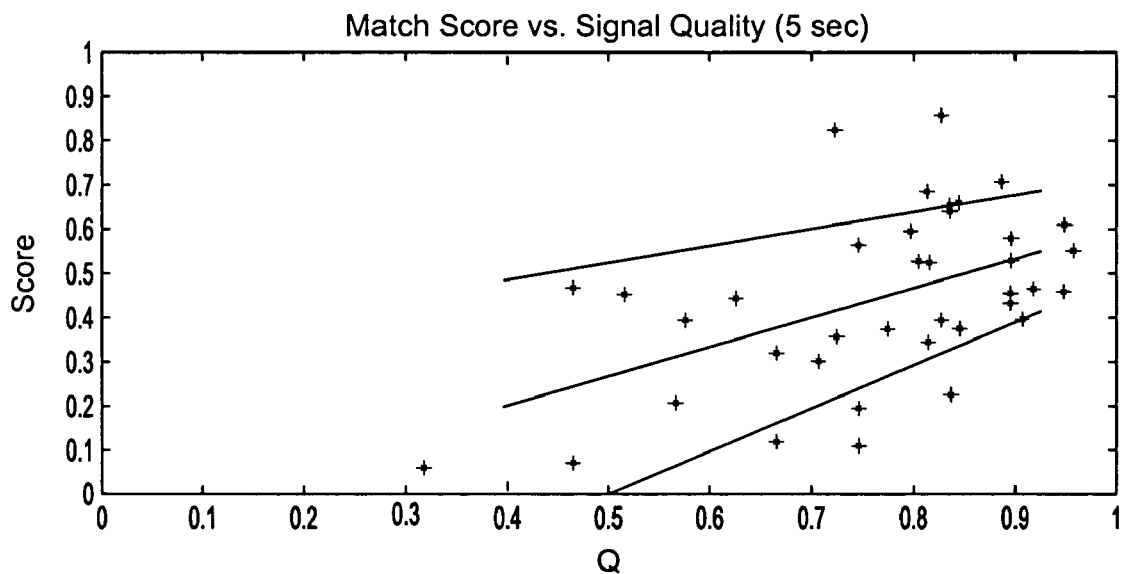
Figure 13: Match score distribution as a function of signal quality (5 sec segments)
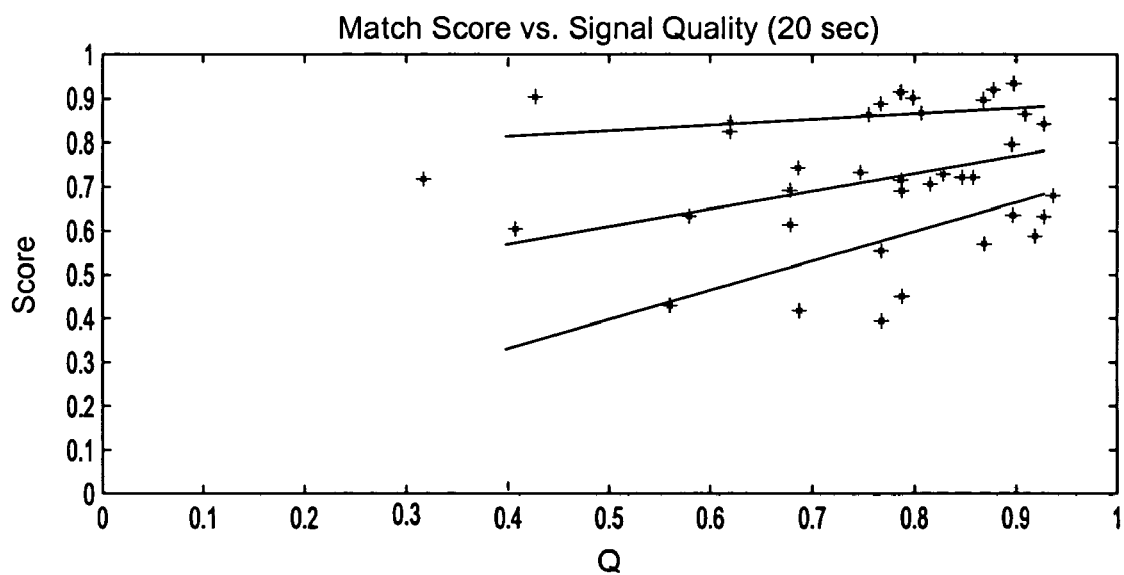
Figure 14:

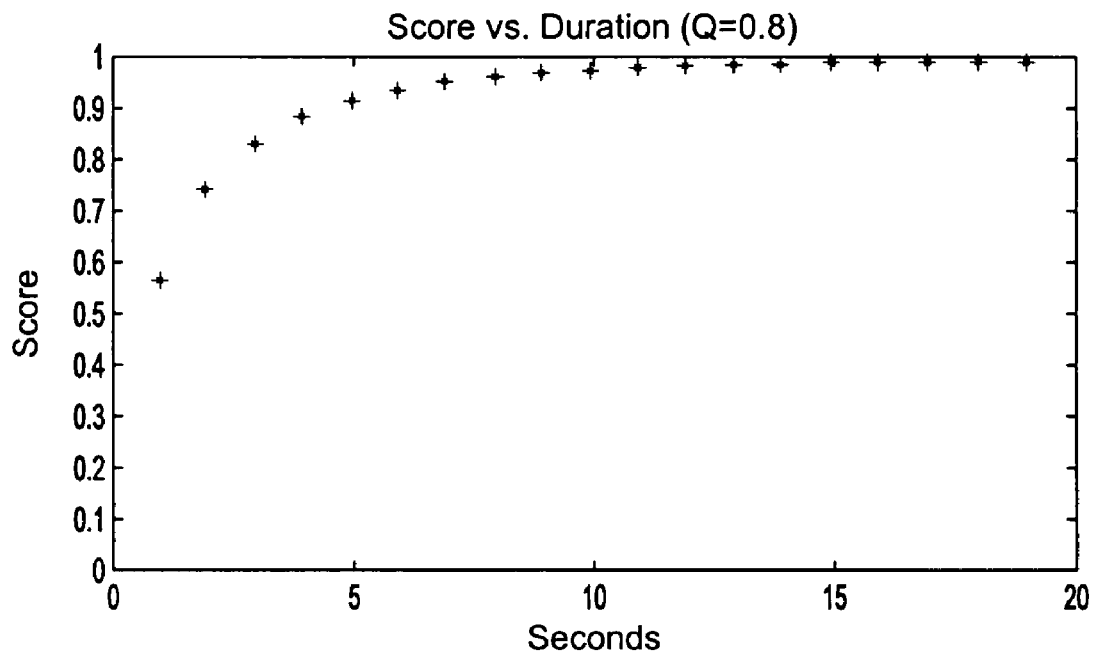
Figure 15: Match score as a function of duration of recording (Q=0.8)
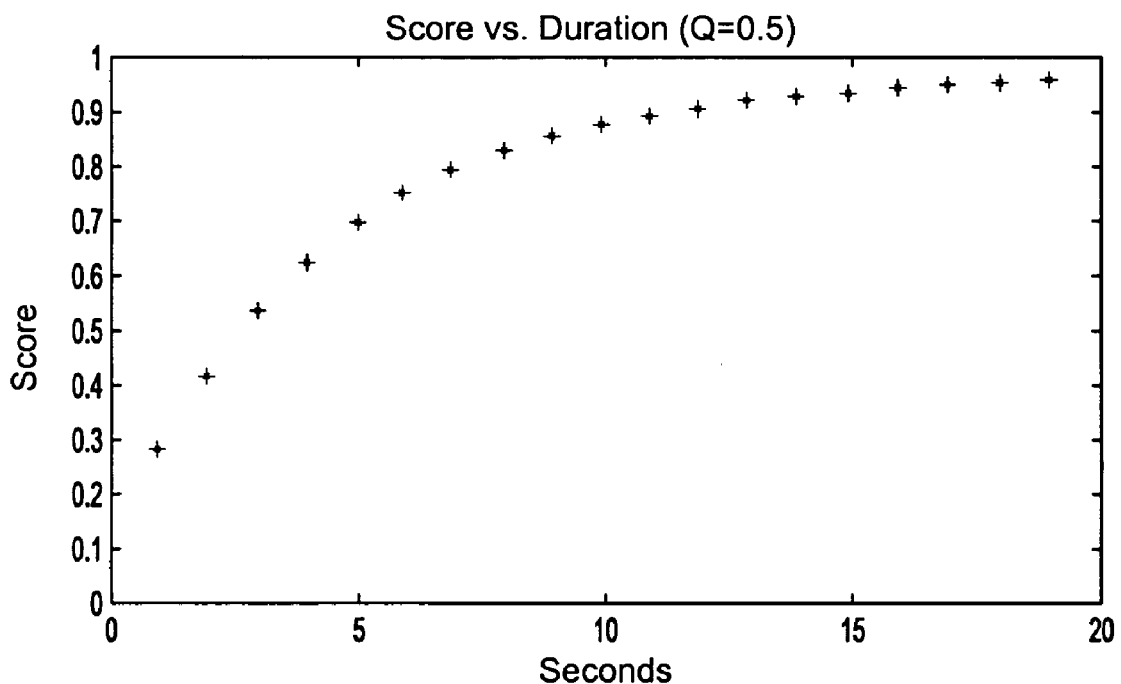
Figure 16

METHOD AND APPARATUS FOR ELECTRO-BIOMETRIC IDENTITY RECOGNITION

CROSS-REFERENCE TO RELATED APPLICATION

This application is a continuation-in-part of, and claims priority to, International Patent Application No. PCT/US2003/023016 filed on Jul. 24, 2003 which claims priority to U.S. Provisional Application 60/398,832 filed on Jul. 29, 2002, the entire disclosures of which are incorporated herein.

BACKGROUND

Identity recognition plays an important role in numerous facets of life, including automatic banking services, e-commerce, e-banking, e-investing, e-data protection, remote access to resources, e-transactions, work security, anti-theft devices, criminologic identification, secure entry, and entry registration in the workplace.

Often computerized systems use passwords and personal identification numbers (PIN) for user recognition. But to maintain security, passwords have to be changed on a regular basis, imposing a substantial burden on the users. Likewise, signature verification methods suffer from other shortcomings, including forgery and enrollment fraud. See for example, U.S. Pat. No. 5,892,824 issued to Beatson et al.

As a result, identity recognition systems that use measures of an individual's biological phenomena—biometrics—have grown in recent years. Utilized alone or integrated with other technologies such as smart cards, encryption keys, and digital signatures, biometrics are expected to pervade nearly all aspects of the economy and our daily lives.

Several advanced technologies have been developed for biometric identification, including fingerprint recognition, retina and iris recognition, face recognition, and voice recognition. For example, Shockley et al., U.S. Pat. No. 5,534,855, generally describes using biometric data, such as fingerprints, to authorize computer access for individuals. Scheidt et al., U.S. Pat. No. 6,490,680, describes identity authentication using biometric data. Dulude et al., U.S. Pat. No. 6,310,966, describes the use of fingerprints, hand geometry, iris and retina scans, and speech patterns as part of a biometric authentication certificate. Murakami et al., U.S. Pat. No. 6,483,929, generally describes "physiological and histological markers," including infra-red radiation, for biometric authentication. However, these types of technologies have penetrated only limited markets due to complicated and unfriendly acquisition modalities, sensitivity to environmental parameters (such as lighting conditions and background noise), and high cost. In addition, due to complicated acquisition procedures, the foregoing technologies usually require operator attendance.

Fingerprint recognition is well-established and the most mature technology of the group. But it has several drawbacks: a fingerprint recognition system cannot verify physical presence of the fingerprint owner and therefore is prone to deception, limiting its suitability for on-line applications; the optical sensor is a costly and fragile device generally unsuitable for consumer markets; and the system suffers from negative connotations related to criminology.

Retina scanning technologies are characterized by high performance. However, they require high-precision optical sensors, and are not user friendly because they require manipulation of head posture and operate on a very sensitive organ—the the human eye. The optical sensor is also costly and fragile.

Iris and face recognition systems are user-friendly technologies since they record an image from afar and are not intrusive. However, they require digital photographic equipment and are sensitive to lighting conditions, pupil size variations and facial expressions. In addition, iris recognition performance is degraded by the use of dark glasses and contact lens, and face recognition may be deceived by impersonation.

Voice recognition is the most user-friendly technology of the group; however, it requires a low-noise setting and is highly sensitive to intrinsically variable speech parameters, including intonation. Moreover, existing conventional recording technologies may be used to deceive speech-based recognition systems.

Thus, a need exists for reliable, robust, hard to deceive (on-line and off-line), low cost, user friendly identity recognition technologies that may be used in stand-alone applications or integrated with existing security systems.

Over the years, electrocardiogram ("ECG") measurements have been used for many different purposes. ECG signals are electric signals generated by the heart and can be picked up using conventional surface electrodes, usually mounted on the subject's chest. ECG signals are made up of several components representative of different functional stages during each heart beat and projected according to the electric orientation of the generating tissues.

Individuals present different, subject-specific detail in their electro-cardiologic signals due to normal variations in the heart tissue structure, heart orientation, and electrical tissue orientation, all of which affect the electro-cardiologic signals measured from the limbs. Numerous types of systems make use of these subject-specific variations.

For example, Blazey-et al., U.S. Pat. No. 6,293,904, describes the use of ECG signals to evaluate or profile an individual's physiological and cognitive state. As to identification, a 2001 conference paper at the 23$^{rd}$ Annual International IEEE Conference on Engineering in Medicine and Biology Society (in Istanbul, Turkey) by Kyoso et al., entitled "*Development of an ECG Identification System*," compares a patient's ECG with previously registered ECG feature parameters for purposes of identification. Wiederhold, U.S. Application No. 2003013509, suggests using directly or remotely acquired ECG signals to identify a subject, "explores" feature extraction for identifying individuals, and provides a "preliminary analysis" of such methods.

But an ECG signal is comprised of ECG components having features that may be common to a group. None of these references describe a system or method that eliminates common features of ECG components to create a signature for subject identification. Thus, there still exists a need for systems and methods with these attributes to identify an individual.

The inclusion of the foregoing references in this Background is not an admission that they are prior art or analogous art with respect to the inventions disclosed herein. All references in this Background section are, however, hereby incorporated by reference as though fully set out herein.

SUMMARY

Applicant provides solutions to the foregoing problems of biometric identification with various apparatuses and methods having several aspects.

In a first aspect, applicant solves each of the foregoing problems of biometric identification through the use of the following method and variations thereof:

producing and storing a first biometric signature that identifies a specific individual by forming the difference between a representation of the heartbeat pattern of the specific individual and a stored representation of common features of heartbeat patterns of a plurality of individuals;

after the producing step, obtaining a representation of the heartbeat pattern of a selected individual and producing a second biometric signature by forming the difference between the heartbeat pattern of the selected individual and the stored representation of the common features of the heartbeat patterns of the plurality of individuals; and comparing the second biometric signature with the first biometric signature to determine whether the selected individual is the specific individual.

A system, according to this aspect, comprises an ECG signal acquisition module, an ECG signal processing module that comprises an ECG signature generator, and an output module.

Thus, according to this first aspect, the systems and methods disclosed herein transform bio-electric signals into unique electro-biometric signatures. The uniqueness of the electro-cardiologic signatures makes the system very difficult to deceive, and the method's inherent robustness makes it ideal for local as well as for remote and on-line applications. In addition, a biometric-signature-based system is characterized by high recognition performance and supports both open and closed search modes.

In one preferred method according to the first aspect, the stored representation of common features of one or more ECG components is obtained by measuring and storing such representations for a plurality of individuals and then averaging all of the stored representations. Alternately, the common features may be obtained through techniques such as principal component analysis, fuzzy clustering analysis, wavelet decomposition, and the like.

Since electro-cardiologic methods according to this first aspect are robust, they have another important advantage: they permit a simple and straightforward acquisition technology that can be implemented as a low-cost, user friendly acquisition apparatus and also eliminate the need for a skilled operator.

According to a variation on these systems and methods, the common features of one or more of subject's ECG components may be removed using an analytical model of common features of one or more ECG components, instead of, or in addition to, use of an empirical model. Likewise, the common features may be removed by first classifying the stored representations into subgroups, identifying the common features in at least one subgroup, classifying a subject signal according to subgroup, creating a subject signature by removing the common features of one or more of the subgroup's ECG components from the subject signal, and identifying the subject by calculating the subject signature correlations relative to that subgroup's signatures.

Multiple templates may also be kept for each subject, such as by storing multiple signatures produced by an individual at different pulse rates. In this embodiment, the subject signature may then be correlated with the appropriate template, such as the one for the appropriate pulse rate. Thus, in a variation, the systems and methods disclosed herein may use multiple signature templates to identify an individual over a range of circumstances and reactions. Alternatively, or in addition, according to the first aspect, the subject signal and the enrolled signals may also be normalized based on pulse rate.

According to a second aspect disclosed herein, a process for identification may set a dynamic threshold. This dynamic threshold may be based on a desired level of confidence in the identification, such as one determined by a confidence score.

According to a third aspect disclosed herein, the systems and methods disclosed herein may employ a "Q-factor" to determine whether to reduce signal contamination due to noise. Likewise, the Q-factor or other quality of signal measurement may be used to determine the length of the subject sample required to identify a subject with a desired level of confidence. It may also be used to enroll a sample with the desired level of confidence so that the sample may be suitable for the future comparison.

In an alternate embodiment to the "Q-factor" calculation, the systems and methods disclosed herein may calculate standard deviations in the subject signature and/or enrolled signatures due to noise, and from those calculations determine whether signal quality is appropriate for identification.

Likewise, the systems and methods disclosed herein may determine the signal quality by measuring the impedance of the contact or probe. Signal quality measurements according to this aspect may also be used to inform the subject to adjust his or her contact with or position relative to the sensor or probe.

According to a fourth aspect, the subject and database signatures may be encrypted as a safety precaution against unauthorized access to and use of the signatures.

According to a fifth aspect, the ECG signal may be acquired with electrodes placed in contact with certain body sites that yield a consistent signal. For certain body locations even a slight change of electrode placement may cause drastic changes in the received signal morphology, and may even cause distinct signal components to appear or disappear. Thus, according to this aspect, the methods and systems disclosed herein may use electrode placement sites that produce subject-specific, consistent signals, that are robust notwithstanding changes of electrode placement within the sites. These sites include the arms and legs (including fingers and toes). The robustness of electrode placement within these sites stems from a constant electro-cardiologic signal projection which does not change as long as the electrodes remain close to a limb extremity.

According to this same fifth aspect, certain sensing probes, known as ultra-high impedance sensing probes, may also be used to acquire a signal, including a signal from a single body point such as a fingertip. Alternately, or in addition, these ultra-high impedance probes may remotely sense the electro-cardiologic signal and thereby eliminate the difficulty of electrode placement while maintaining signal consistency.

According to a sixth aspect, the systems and methods disclosed herein may comprise elements and steps that protect against enrollment fraud and reduce the ability of a database enrollee to misrepresent his or her identity.

According to a seventh aspect, the systems and methods disclosed herein may identify a subject by comparing his or her match scores with the match scores of database enrollees.

According to an eighth aspect, the systems and methods disclosed herein may use weighted correlation techniques, ascribing different weights to different electro-cardiologic signal components for the purpose of producing a signature. Alternatively, or in addition, signatures may be normalized using a variety of metrics including root-mean-square computations or L1 metrics.

The systems and methods according to each of the foregoing aspects preferably perform their tasks automatically for the purpose of identity recognition. Further, these systems and methods can be incorporated into a wide range of devices and systems. A few non-limiting examples are as follows: a smart card; a passport; a driver's license apparatus; a Bio-logon identification apparatus; a personal digital assistant ("PDA"); a cellular-embedded identification apparatus; an anti-theft apparatus; an ECG monitoring apparatus; an e-banking apparatus; an e-transaction apparatus; a pet identification apparatus; a physical access apparatus; a logical access apparatus; and an apparatus combining ECG and fingerprint monitoring, blood pressure monitoring and/or any other form of biometric device.

Further, the systems and methods disclosed herein can be used to identify a person's age, such as by comparing the width of a subject's QRS complex, or more generally the subject's QRS-related signature component, with those of an enrolled group or analytical ECG model.

In another application, the systems and methods herein may be used to identify persons on medication, such as by enrolling and calculating, or analytically deriving, a series of drug-related signature templates. This method may also be used to identify or catch subjects who would attempt to fool the system by using medication to alter their ECG signal.

Other applications include using the systems and method disclosed herein for building and room access control, surveillance system access, wireless device access, control and user verification, mobile phone activation, computer access control (including via laptop, PC, mouse, and/or keyboard), data access (such as document control), passenger identification on public transportation, elevator access control, firearm locking, vehicle control systems (including via ignition start and door locks), smart card access control and smart card credit authorization, access to online-line material (including copyright-protected works), electronic ticketing, access and control of nuclear material, robot control, aircraft access and control (passenger identity, flight control, access of maintenance workers), vending machine access and control, laundromat washer/dryer access and control, locker access, child-proof locks, television and/or video access control, decryption keys access and use, moneyless slot machines, slot machine maintenance access, game console access (including on-line transaction capability), computer network security (including network access and control), point-of-sale buyer identification, on-line transactions (including customer identification and account access), cash payment service or wire transfer identification, building maintenance access and control, and implanted medical device programming control. Other applications will be apparent to those skilled in the art and within the scope of this disclosure.

For any application, an apparatus according to any or all of the foregoing aspects can operate continuously or on demand. The apparatus can be constructed to obtain the representation of the heartbeat pattern of a selected individual by having one or more electrodes in contact with individual or sensors remote from the individual. When the apparatus is provided in a smart card, the card can be enabled for a limited period of time after successful recognition and disabled thereafter until the next successful recognition is performed. The apparatus can be constructed to operate with encryption keys or digital signatures.

As to the methods disclosed herein, the steps of the foregoing methods may be performed sequentially or in some other order. The systems and methods disclosed herein may be used on human or other animal subjects.

Each of these aspects may be used in permutation and combination with one another. Further embodiments as well as modifications, variations and enhancements are also described herein.

BRIEF DESCRIPTION OF THE DRAWINGS

FIG. 1 is a simplified block diagram of a system for use with the aspects disclosed herein composed of a signal acquisition module, a signal processing module, and an output module.

FIG. 2 is a block diagram of an embodiment of the signal acquisition module of the system of FIG. 1.

FIG. 3 is a block diagram of an embodiment of the signal processing module of the system of FIG. 1.

FIG. 4 is a diagram showing a grand-average electro-cardiologic signal waveform calculated from a database of 20 subjects.

FIG. 5 shows a group of electro-cardiologic signal waveforms of ten of the subjects participating in the database and contributing to the average waveform of FIG. 4.

FIG. 6 shows a group of electro-biometric signature waveforms, or templates, derived from the signal waveforms of FIG. 5.

FIG. 7 shows a scatter plot and distribution histograms of the sign-maintained squared correlation values of the 20 subjects who contributed to the grand average waveform of FIG. 4.

FIG. 8 shows a table of z-scores based on the desired degree of confidence in the identification cut-off.

FIG. 9a shows a distribution of correlation.

FIG. 9b shows a distribution of Z-transformed correlations.

FIG. 10 shows identification performance curves (static).

FIG. 11 shows identification performance curves (dynamic).

FIG. 12 shows signal quality as a function of NSR.

FIG. 13 shows match score distribution as a function of signal quality for 5 second segments.

FIG. 14 shows match score distribution as a function of signal quality for 20 second segments.

FIG. 15 shows match score as a function of recording duration (for Q=0.8).

FIG. 16 shows match score as a function of recording duration (for Q=0.5).

DETAILED DESCRIPTION

Definitions

Figure 17:
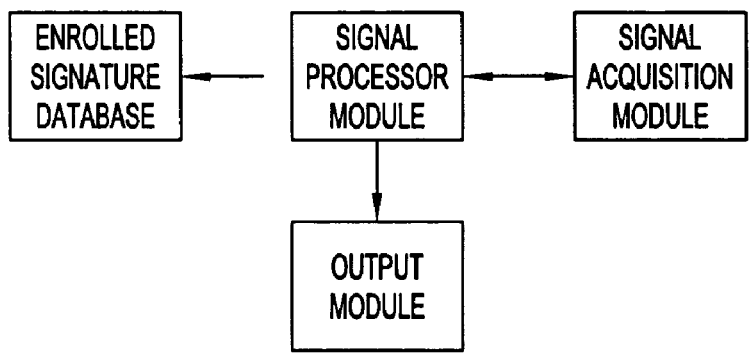
FIG. 17 shows a functional component diagram of a preferred system.

Unless otherwise indicated, the meaning of the terms "identify," "identifying" and "identification" include the concepts of "verify identity," "verifying identity," and "verification of identity," respectively.

"Closed search" means a search in which a single stored signature is examined to verify the identity of an individual.

"Open search" means a search in which a plurality of stored signatures are searched to identify a subject.

First Aspect:

According to the first aspect, a bio-electric signal is acquired, processed and analyzed to identify the identity of an individual. A preferred embodiment of a system and a method according to this first aspect is illustrated, by way of example, in FIG. 1. FIG. 1 shows a system called an Electro-Biometric IDentification (E-BioID) system. In this preferred embodiment, the stored representation of the common features of the one or more ECG components of the plurality of individuals is the average of those individuals' one or more ECG components. However, other embodiments can utilize stored representations of different types of common features, such as those attainable by, for example, principal component analysis, fuzzy clustering analysis, or wavelet decomposition, or provided by an analytical model.

In the preferred embodiment, the basic elements of the E-BioID system include a signal acquisition module 12, a signal processing module 14, and an output module 16, implemented in a single housing. In another preferred embodiment, the system may provide for remote analysis of locally acquired electro-biometric signals. Each of the components shown in FIG. 1 can be readily implemented by those skilled in the art, based on principles and techniques already well known in the art in combination with the present disclosure.

FIG. 2 shows a preferred construction of the signal acquisition module 12 in an E-BioID system. The data acquisition module preferably includes one or more sensors 22, pre-amplifiers 24, band-pass filters 26 and an analog-to-digital (A/D) converter 28. Each of these components can be readily implemented by those skilled in the art, based on principles and techniques already well known in the art in combination with the present disclosure.

Sensors 22 can be of any type capable of detecting the heartbeat pattern. For example, they can be metal plate sensors that are an "add-on" to a standard computer keyboard. According to another aspect, a single sensor may, by itself, acquire the signal from a single point of contact, such as by contacting a finger; alternately, the sensor may not need to touch the subject at all.

FIG. 3 shows preferred elements of signal processing module 14 in the E-BioID system. The signal processing module preferably includes a Digital Signal Processor (DSP) 32, a Dual Port Ram (DPR) 34, an Electrically Erasable Programmable Read Only Memory ($E^2$PROM) 36 and an I/O port 38. Each of these components can be readily implemented by those skilled in the art, based on principles and techniques already well known in the art in combination with the present disclosure. Signal processing module 14 is connected to signal acquisition module 12 and output module 16 via port 38.

In an alternative embodiment, the signal processing module may be implemented, with suitable programming, on a personal computer, which is a flexible computation platform, allowing straight-forward integration of the system into existing computing facilities in a home, office, or institute/enterprise environments.

Output module 16 preferably consists of a dedicated display unit such as an LCD or CRT monitor, and may include a relay for activation of an external electrical apparatus such as a locking mechanism. Alternatively, the output module may include a communication line for relaying the recognition result to a remote site for further action.

Signal Acquisition, Processing and Analysis

Bioelectric signals, or heartbeat signals, are acquired in a simple manner, where the subject is instructed to touch at least one sensor 22 for a few seconds. The one or more sensors, which may be metal plates, conduct the bioelectric signals to the amplifiers 24, which amplify the bioelectric signals to the desired voltage range. In a preferred embodiment, the voltage range is zero to five volts.

The amplified signals pass through filters 26 to remove contributions outside a preferable frequency range of 4 Hz-40Hz. Alternatively, a wider range of 0.1 Hz-100 Hz may be used in conjunction with a notch filter to reject mains frequency interference (50/60 Hz). Digitization of the signal is preferably performed with a 12-bit A/D converter 28, at a sampling frequency of preferably about 250 Hz.

In module 14, the signals are normalized by the 'R' peak magnitude, to account for signal magnitude variations which mostly relate to exogenic electrical properties. The normalized data is transformed into an electro-biometric signature which is compared to pre-stored electro-biometric signature templates. The result of the comparison is quantified, optionally assigned a confidence value, and then transmitted to output module 16, which provides recognition feedback to the user of the E-BioID system and may also activate external apparatuses such as a lock or siren, virtual apparatuses like network login confirmation, or a communication link.

Alternately, or in addition, the signal may be normalized for pulse rate. This is useful because electro-cardiologic signals are affected by changes in pulse rate, which is a well-known electro-cardiologic modifier. Pulse rate changes may cause latency, amplitude and morphological changes of the 'P' and 'T' components relative to the 'QRS' component of the electro-cardiologic signal (these components appear in FIG. 5). However, pulse rate changes may be automatically compensated for by retrospective, pulse rate-driven adjustment of the signal complex. Moreover, an adaptive operation mode of the system can track and compensate for pulse rate induced changes. This can be done by compressing or expanding the time scale of one cycle of the heartbeat waveform. More sophisticated formulations describing the relations between waveform characteristics (e.g. S-T, P-Q segment durations) and pulse rate may be used. Thus, a method according to this variation may be based on electro-cardiologic signal discrimination, wherein analysis is carried out synchronously with the heart beat, eliminating features common to the general population and thus enhancing subject-specific features that constitute an electro-biometric, or biometric, signature, normally undetectable in raw electro-cardiologic signals.

In another embodiment, the E-BioID system is implemented as a fully integrated compact device, where many of the functional elements are implemented on an ASIC based system.

In another embodiment, the apparatus can be incorporated into a watch worn on the wrist, where the signal is, measured between the wrist of the hand on which the watch is worn and the other hand of the wearer. The back side of the watch may be made of a conductive medium (e.g. a metal plate) in contact with the back of the wrist, and the face of the watch can be provided with another metal contact that needs to be touched with a finger of the other hand. The watch may transmit a signal indicating confirmation of the identity of its wearer, and/or activating a physically or logically locked device such as a door, a computer, a safe, etc. The watch may also transmit personal information about its wearer.

Principle of Operation

Biometric recognition requires comparing a newly acquired biometric signature against signature templates in a registered or enrolled biometric signature template database. This calls for two phases of system operation: Enrollment and Recognition.

Enrollment Phase

In a preferred embodiment, each new subject is instructed to touch a first sensor with a finger of the left hand, while simultaneously touching another sensor with a finger of the right. In alternative embodiments, the subject may touch the sensors, typically made of metal, with other parts of the body, preferably the hands or legs. In another embodiment, the subject may touch a single sensor with a single body point. Alternately, the subject need not touch a sensor at all. The system monitors the subject's pulse rate and initiates a recording, preferably lasting for at least 20 seconds. Shorter intervals may be used depending on the required level of accuracy. Once the recording is complete, the system may perform a self-test to verify signature consistency by comparison of at least two biometric signatures derived from two parts of the registered segment. The two parts may be two halves, or two larger, overlapping, segments. The two parts may be used to derive two biometric signatures. If the self-test result is successful, enrollment of that subject is complete, and if unsuccessful the procedure is repeated. The successful recording is used for construction of an electro-cardiologic signal or a series of electro-cardiologic signals, which are added to an electro-cardiologic signal database.

The electro-cardiologic signals are then transformed into a set of electro-biometric signature templates by eliminating features that are common to all or a subset of the subjects participating in the dataset, thereby enhancing subject-specific discriminating features.

In a preferred embodiment, the system creates a grand-average electro-cardiologic template, which is calculated by synchronous averaging of normalized electro-cardiologic signals from the entire pool of subjects. The grand-average represents the above-mentioned common features, and thus subtraction of the grand-average from each one of the electro-cardiologic signals yields a set of distinct, subject-specific electro-biometric template signatures. In an alternative embodiment, other means for elimination of the common features may be used, such as a principal component analysis, fuzzy clustering analysis or wavelet decomposition.

Alternately, or in addition, common features may be removed by using an analytical model for common features of one or more ECG components rather than by using an empirical model calculated from the enrolled data.

In another preferred embodiment, the database is divided into several subsets in a way that enhances intra-subset similarity and inter-subset disparity. The embodiment then calculates a distinct grand-average or other common feature determination for one or more of the subsets. This database partition itself may be performed using standard pattern classification schemes such as linear classifiers, Bayesian classifiers, fuzzy classifiers, or neural networks. In case of a large database, it is useful to partition the database into subsets in order to simplify and shorten the search process as well as to ensure the validity of the grand-average as an appropriate representative of similarity among the electro-cardiologic signals. The subject signature may then be created by removing common features found in the appropriate subgroup.

FIG. 4 shows an example of a grand-average, constructed from a pool of 20 subjects participating in the database.

FIG. 5 shows 10 examples of electro-cardiologic signals, and FIG. 6 shows the electro-biometric template signatures derived from the above electro-cardiologic signals by elimination of features common to all the subjects included in the database. Specifically, each signature of FIG. 6 is obtained by subtracting the waveform of FIG. 4 from the corresponding signal of FIG. 5. It will be observed that while the original electro-cardiologic signals are highly similar, the derived electro-biometric signatures are markedly different. These differences have been found to reflect inherently unique electro-cardiologic disparity which underlies the recognition capabilities of the E-BioID system.

Recognition Phase

In the recognition phase, the subject interacts with the system in a similar manner to that of the enrollment phase, however a shorter recording time on the order of a few seconds is sufficient.

In a preferred embodiment, the system executes a verification procedure (closed search): the system processes the acquired signals, forms an electro-biometric subject signature by removing common features found in the entire database, found in a partitioned subgroup of the database or provided by analytical ECG model, adjusts the signature according to the pulse rate, and compares the adjusted electro-biometric signature with the subject's enrolled electro-biometric signature template.

In another preferred embodiment, the system executes an identification procedure (open search): the system repeats the comparison process for the entire database or a partitioned sub-group of the database, thereby providing identification of the matching identity.

The Comparison Process

In a preferred embodiment, the comparison is performed by calculation of a correlation coefficient, $\rho$, between an electro-biometric signature $\sigma_j$ and an electro-biometric signature template $\Phi_i$, as follows:

$$\rho = \frac{COV[\sigma_j, \Phi_i]}{\sqrt{VAR[\sigma_j] \cdot VAR[\Phi_i]}}.$$

The correlation coefficient is squared, maintaining its original sign: $\eta = sign(\rho)*|\rho|^2$. In an alternative embodiment, the comparison may be based on other similarity measures, such as RMS error between the electro-biometric signatures.

The comparison may yield one or several correlation coefficients, depending on the mode of operation: closed search; or open search. In a closed search mode, the sign-maintained squared correlation coefficient ($\eta$) is used for making the recognition decision: a value greater than a preset threshold is regarded as a positive identification, or a match; borderline, near-threshold values may indicate a need for extended or repeated recording. In an open search mode, the largest sign-maintained squared correlation coefficient among all sign-maintained squared correlation coefficients yields the most likely subject identification, provided that the highest coefficient is above a selected threshold.

The preset threshold is derived from the required confidence level; higher desired confidence levels require higher thresholds. In one embodiment, sign-maintained squared correlation values larger than 0.8 are characteristic of a match and values lower than 0.7 are characteristic of a mismatch. Thus, sign-maintained squared correlation values higher than 0.8 may be considered as true matches and values lower than 0.7 as mismatches.

The upper diagrams of FIG. 7 shows a scatter plot of sign-maintained squared correlation values, marking the 0.8 threshold with a dashed line. A clear separation between matches (circles) and mismatches (stars) is evident. The histograms in the other two diagrams provide a different view of the powerful recognition capabilities of the E-BioID system, where it can be seen that the mismatches are concentrated around the zero value (no correlation) while matches are densely distributed near 1.0 (absolute correlation).

In alternative embodiments, more sophisticated decision schemes may be used such as multi-parameter schemes (e.g. fuzzy logic schemes), which use more than one distance measure; for example, multiple correlation values can be derived from segmented data analysis.

In a preferred embodiment, the system improves its performance with time by adding electro-cardiologic signals to the subject's database file when changes in the signals are encountered. In subsequent recognitions, the system processes the newly acquired signals, calculates the pulse rate, forms an electro-biometric subject signature, selects the enrolled electro-biometric signature template with the most similar pulse rate, and compares the new electro-biometric signature with the selected enrolled electro-biometric signature template.

In another preferred embodiment, the system uses signals acquired during long-term system operation to track possible variation in the enrolled subject electro-cardiologic signal and, if consistent changes occur, the enrolled signal is automatically adjusted to reflect these changes. This tracking process compensates for gradual changes in the electro-cardiologic signal over long time periods, but does not compensate for fast, acute changes like those expected in connection with clinical heart conditions. In another embodiment, such acute changes may be reported to the subject indicating a need for medical consultation.

Second Aspect:

Biometric identification methods benefit from proper determination of an identification threshold. The identification threshold may be derived from correlation analysis between candidate signatures and registered database signatures. The threshold may be determined using a distribution of empirical data to achieve optimal identification performance. Yet a fixed threshold implicitly assumes deterministic signatures and stationary noise, while in practice signatures are variable and noise depends on mostly unpredictable external influences. Therefore, biometric identification methods, including those according to the first aspect, may be adversely affected by signal and noise variations in database and test readings. In general, this would yield decreased correlations for both matches and mismatches.

Thus, according to the second aspect, methods and systems of biometric identification, including those according to the first aspect, may use a dynamic threshold capable of compensating for the effect of signal variations and noise interference. This aspect yields a dynamic, data-dependent identification threshold. In the preferred embodiment, the dynamic threshold is re-calculated in each identification attempt using a statistical approach to normalize the correlation data and thus enable calculation of a quantifiable, statistically significant identification threshold. The threshold is shown to be resistant to variable signal and noise conditions.

The preferred method according to this second aspect is based on determination of a confidence limit for a correlation-based scoring between a test signature and a set of registered signatures. A confidence limit describes, with a given degree of statistical confidence, the upper and lower limits for the values in question. A two-tailed limit describes both upper and lower bounds, while a one-tailed limit describes only an upper or a lower cutoff, with the understanding that there is either no lower or no upper limit to the value of the variable. Confidence limits can be determined statistically, in several different ways, if the variable under consideration meets certain statistical criteria appropriate to each statistical method.

Most statistical methods rely on the values of a normally distributed variable, that is, according to the bell-shaped Gaussian distribution. Normally distributed variables have been well characterized statistically, and their statistical limits can be determined in a straightforward manner based on the variable average and variation.

When a variable is not distributed normally, a normalizing transformation may be used to transform the original variable into a new variable which would then be distributed normally, and may thus be used to determine confidence limits. The appropriate mathematical transformation may be determined using statistical considerations, or by empirical examination of a sufficiently large dataset. In order to express the confidence limits in terms of the original variable, a back-transformation is also required.

Signal cross-correlation analysis may be used for the matching procedure. Values range from −1 (absolute negative correlation) through 0 (no correlation) to +1 (absolute positive correlation). Generally, significantly positive correlation indicates a probable true identification, and thus a one-tailed, upper confidence limit should be used to describe the dynamic identification threshold.

By definition, correlations are bounded variables and thus are not normally distributed. A mathematical transformation is necessary to normalize the correlation distribution allowing determination of the upper confidence limit. Alternatively, empirical techniques which do not rely on such transformations may be used.

A preferred method, described more fully below, is particularly appropriate for correlation analysis. It is based on the Fisher Z transformation, which converts correlations into a normally distributed variable.

Another method may use squared correlations. Since raw correlations are not additive, averages or other statistical functions of correlations have no statistical meaning. Squared correlations are additive, but they are also not normally distributed, so that additional transformations would be required. If prior processing of the correlations changes the distribution of their values, additional transformations may be necessary to account for these changes. These additional transformations include, but are not limited to, logarithms, squares, square roots, and transcendental functions.

Still another method would involve a degree of prior empirical testing, preferably where a large number of candidates are correlated to a large database. The likelihood of false identifications would be directly determined by examination of this database, or appropriate transformations could be empirically determined. However, because this method is not dynamic and must be performed prior to real testing, the effects of testing conditions cannot be easily compensated, requiring development of mathematical models for the influence of noise.

The preferred method according to this second aspect, the Fisher-transform method, involves transformation of the correlations between the candidate signature and the registered signatures in order to obtain a distribution of scores that are more nearly normally distributed. As noted above, data that meets assumptions of normality can be used to derive parametric confidence limits.

The Fisher Z transformation was designed to normalize correlations. The transformation may be expressed as follows:

$$Z_f = \text{arc tan } h(r)$$

Where $Z_f$ is the transformed value, arctanh is the hyperbolic arc tangent function, and r is the correlation. The arctanh should be expressed in radians.

Once all the correlations are transformed, a one-tailed confidence limit for the transformed scores may be determined by taking the mean of all the transformed correlations and the standard deviations of all the transformed correlations, with the exception of the candidate correlation, and calculating:

$$\text{Confidence limit} = \tanh(Z_{f\,mean} + z \cdot sd_{Zf})$$

where z is the normal distribution 'z score', $Z_{f\,mean}$ is the mean of transformed correlations with the database, and $sd_{Zf}$ is the standard deviation of the transformed correlations with the data base.

The lower case z here refers to the value of the normal distribution z-score, which is derived based on the desired degree of confidence in the cut-off. A table of such scores is provided in FIG. 8.

In the table of FIG. 8, the standard deviation is multiplied by the appropriate z-score and is added to the mean, and the entire quantity back-transformed to a correlation by taking the hyperbolic tangent.

For example, a 95% confidence limit could be determined using a z score of 1.65. So if the mean of the transformed values was 0.05, and the standard deviation was 0.25, the 95% confidence limit would be 0.72. That is, a correlation value over. 0.72 would only occur by chance less than 5% of the time.

A reverse procedure is used to determine the likelihood that any specific candidate identification is due to random chance. By solving for the z-score:

$$z = (Z_{fc} - Z_{f\,mean}) / sd_{Zf}$$

where z is the normal distribution 'z score', $Z_{fc}$ is the transformed candidate correlation, $Z_{f\,mean}$ is the mean of transformed correlations with the database, and $sd_{Zf}$ is the standard deviation of the transformed correlations with the data base.

The resulting z-score can be converted to a 1-tailed probability value by reference to a table of the cumulative normal distribution, and interpolation if necessary. For example, with reference to the abbreviated table above, a z-score of 1.80 would suggest a 3.75% probability that the candidate correlated so highly by chance.

As mentioned above, if noise in the registered signatures or in the candidate signature is random, it would reduce the overall correlations with the candidate value. The true identification, if it exists, would therefore have a lower correlation with the candidate. It should be noted that variability of raw correlations increases as the raw values decrease, since high raw correlations are less variable due to a ceiling effect of maximum correlation of 1, but this is compensated for by the transformation. Thus, a dynamic threshold with the desired certainty may be re-calculated in each identification attempt using the foregoing methods. Importantly, overall random noise still tends to drive all correlations toward zero and reduce overall true variability, thereby lowering the confidence limit accordingly; yet a true match would remain significant as long as the signal to noise ratio does not fall below a certain limit.

The following examples of the second aspect are based on a 38-subject database. All subjects are healthy individuals, participating in the study on a voluntary basis.

EXAMPLE 1

Normalization of Correlations

A set of 703 cross-correlations was obtained by correlating all pairs in the database. The raw and z-transformed correlation distributions are presented in FIG. 9. While raw correlations are not normally distributed (top), the transformed correlations appear to represent a near-normal distribution (bottom).

EXAMPLE 2

Performance

The biometric identification method was implemented using analysis of 38 enrolled signatures and 38 test signatures. FIG. 10 presents FAR and FRR performance curves as a function of a static threshold, and FIG. 11 presents the performance curves as a function of a dynamic threshold. Clearly, the dynamic threshold provides significantly superior results (eg. $EER_{Static} = 3\%$, $EER_{Dynamic} = 0\%$).

Third Aspect:

As described above, the dynamic identification threshold is a data-driven threshold, preferably re-calculated in each identification session to establish a confidence limit and substantiate a statistical significance of the identification process. Yet overall scores still decrease with the drop in signal quality due to background noise, lowering the dynamic threshold and thereby reducing identification confidence. This problem calls for assessment of signal quality in both enrollment and identification phases to facilitate high performance recognition.

The third aspect solves this problem by calculation of a Q value—a type of signal quality index. A quality of signal index Q is a quantitative description of the quality of the ECG signature. It is based on an analysis of the random error in two or more ECG complexes, derived with reference to their signal average ECG.

The Q value may be used to confirm signal quality during the enrollment and identification phases, ensuring adequate system performance. In case of a Q factor lower than required by a predefined threshold (itself based on the desired level of identification confidence) the measurement may either be extended or repeated until the confidence requirement is met.

One preferred methodology derives Q in a series of steps:

(1) The input ECG signal is segmented into ECG complexes comprised of the conventional wave morphology features (e.g. P, Q-R-S, T elements).

(2) The ECG complexes are aligned ("time-locked") relative to the R wave peak.

(3) An average ECG is derived from the aligned ECG complexes. The preferred method is to take an arithmetic mean, although other methods may be employed, such as the harmonic mean, geometric mean, weighted mean, or median. Other alternatives include transforming the original signals by other methods such as by Principal Component Analysis.

(4) Each original ECG complex is processed relative to the average ECG, such that some difference is derived against the average ECG. The preferred method is to perform subtraction, i.e. original ECG minus average ECG, although other methods may be employed (e.g. division of the original ECG by average ECG). If the average ECG is a stable and true representation of the subject's ECG, then the resulting difference is a representation of the noise inherent in each individual ECG complex (ECG noise).

(5) Each sample point which corresponds in time across each ECG noise complex is processed together to derive a measure of variability. The most preferred method is to determine the variance. Other measures that may be employed include standard deviation or range.

(6) An average is taken of these measures of variability. The most preferred method is to take an arithmetic average. Other methods may involve taking averages after transformation (e.g. log), or taking alternative averages (geometric, harmonic, median). Other summary scores may also be employed, such as the maximum.

Noting that the signal may be normalized prior to analysis, the average may itself be employed as a Q index, as it is directly related to the SNR. Alternatively, various other scaling transformations may be applied to the average to convert it to an index with the desired minima, maxima, and linearity characteristics.

Example 1 According to the Third Aspect: Q (Signal Quality) vs. NSR (Noise to Signal Ratio)

If X denotes the ECG data matrix, each row representing one ECG complex may be denoted $x_i(n)$ where i is the index of an ECG complex and n represents a discrete time unit. The average of all ECG complexes is denoted $\underline{x}(n)$. For every point in time n we calculate the error term: $e_i(n)=x_i(n)-\underline{x}(n)$, whose variance shall be denoted: $\sigma_e^2(n)$. A preferred scaling conversion, transforming the average of variability into a zero to one range is defined as follows:

$$Q=(1+100*\underline{\sigma}_e^2(n))^{-0.5}$$

A simulation shown in FIG. 12 demonstrates the utility of using the above Q factor to assess the signal to noise level. This simulation uses real-life ECG recordings with increasing levels of Gaussian white noise added to the signal. FIG. 12 presents Q values as a function of the Noise to Signal Ratio (NSR). It can be seen that once Q starts to decline from its plateau, it drops monotonically with the increase in NSR, until the ECG alignment procedure breaks down (NSR~−35 dB, Q~0.2).

Example 2 According to the Third Aspect: Score as a Function of Signal Quality

In theory, match scores close to 1 indicate a positive match, while non-match scores should tend to zero indicating complete lack of correlation. In practice, however, true match scores are influenced by temporal variations in the ECG signature and, more significantly, from background noise. Thus, a higher signal quality is required for short time, high scored identification. It should be noted that high quality signal increases the upper bound on match score, but does not influence the lower bound which depends on the cardiologic signature variability. The example represented by FIGS. 13 and 14 demonstrates score distribution as a function of signal quality, based on a database of 38 subjects. FIG. 13 shows short data segments of 5 seconds each. In contrast, FIG. 14 shows longer segments of 20 seconds each (FIG. 14). Obviously, with longer segments the effect of noise is compensated to some extent and the score distribution flattens.

Example 3 According to the Third Aspect: Signal Quality and Duration of Recording Signal quality may be quantified using the Q parameter. With smaller Q values, and provided that Q does not fall below a certain limit where the ECG alignment process breaks down, longer recordings are necessary to maintain a certain level of statistical significance. FIGS. 15 and 16 show the increase in identification score as a function of the length of recording for a given Q value.

Thus, according to this third aspect, the methods and systems disclosed herein may calculate signal quality using a Q-factor or other measure, and cause the system to seek a sample with reduced noise or to take a longer sample based on the Q-factor or other signal quality measure and the desired degree of identification confidence.

Fourth Aspect:

According to a fourth aspect, the methods and systems disclosed herein may encrypt stored signatures. This safety feature is designed to prevent misuse of the data in the database notwithstanding that the various methods and systems herein typically operate on stored signatures rather than raw ECG data. Thus, an added layer of security may be employed by encrypting the signatures themselves. To that end, a variety of scrambling techniques may be used including the PKI (public key infrastructure) techniques used for credit card data. This fourth aspect makes improper use of the enrolled subject's data all the more difficult, since an unauthorized person would have to decrypt the signature and then still need to convert the signature back into a raw data signal, an impossible task without knowing which common features were removed from the raw data. Thus, one advantage of the systems and methods disclosed herein is that they make it extremely difficult for anyone to misuse the stored information.

Fifth Aspect:

Biometric identification systems are in general vulnerable to enrollment fraud. The systems and methods according to this fifth aspect solve this problem by using ECG data from genetically related individuals who have enrolled in the database. Immediate family members often have ECGs that share common features. By correlating a subject's signature with the general population and/or with those enrollees he or she is purportedly related to, the system can confidently determine whether or not the subject is who they purport to be. This technique can be used in addition to confirming the individual's identity through conventional methods such as picture identification and/or fingerprint matching. However, unlike those methods, which are non-Euclidian and not amenable to clustering based on similarity, this technique can determine fraud at any stage of enrollment process by determining a probability of a genetic relationship based on the enrollee's ECG signature.

Sixth Aspect:

The systems and methods disclosed herein may also make use of ultra-high impedance probes to measure ECG. Since reliability and ease of use is important for an ECG-based biometric identification system, it is advantageous to measure an ECG at a single point, or even without touching the subject. Electric potential probes can work with biometric methods and systems, including those described herein, to increase reliability and ease of use for biometric identification. Ultra-high impedance probes come in a variety of forms. See e.g. Electric potential probes-new directions in the remote sensing of the human body, Harland et al., Meas. Sci. Technol. 13 (2002) 163-169. The ultra-high input impedance probes according to this aspect preferably have ultra-low noise characteristics, and do not require a current conducting path in order to operate. As a result, they work well with the foregoing methods and systems even when used by a layperson without the help of an expert system operator. Thus, these probes may be used in airport-based biometric identification systems, such as by acquiring an ECG signal when an individual passes through a scanner (similar to a metal detector) in full dress. Likewise, a single probe may be used to collect an ECG from an individual's finger tip, such as at an ATM or gaming machine. The use of a single probe contact gives the subject more freedom of movement and makes it easier for him or her to comply with the identification and enrollment regimen. This is particularly useful when the biometric identification systems described herein are used to control the subject's operation of machinery, especially when the machine requires physical contact to operate (e.g., a firearm or vehicle). The single probe and remote probe ECG capture systems according to this aspect may also be complemented by noise reduction strategies to reduce body noise and EMG.

Seventh Aspect:

According to a seventh aspect, a biometric identification method and system may correlate the match scores for a subject (which are created by comparing the subject's signature with those of database enrollees) with the match scores of a plurality of enrollees (which are created by comparing the enrollees' signatures with those of database enrollees). Thus, rather than analyzing a distribution of a subject's correlated match scores, this identification technique analyzes the distribution of the correlation of a subject's match scores and those of the enrollees. As with the fifth aspect, the methods and systems according to this aspect are useful for identifying related individuals. This is because an individual related to a group of enrollees will have a Gaussian distribution of match scores that has a substantially higher median than a Gaussian distribution of the match scores for an individual unrelated to the enrollees. Thus, by examining the distribution of match scores, the probability of a subject's genetic relationship with the enrollees may be confirmed.

Eighth Aspect:

Finally, in the alternative or in addition to the correlation techniques described above, the methods and systems described herein may employ a weighted correlation for identification. According to this aspect, the correlation may give different weights to various signature differences. For example, signature differences due to QRS complex features may be weighted more than signature differences due to T or P complex features. The systems and methods may also use the root mean square of the signature values as part of a weighting function since T is highly variable, QRS is stable, and P is somewhere in the middle. Thus, the signatures may be normalized using root-mean-square computations, L1 metrics or another normalizing technique.

Figure 18:
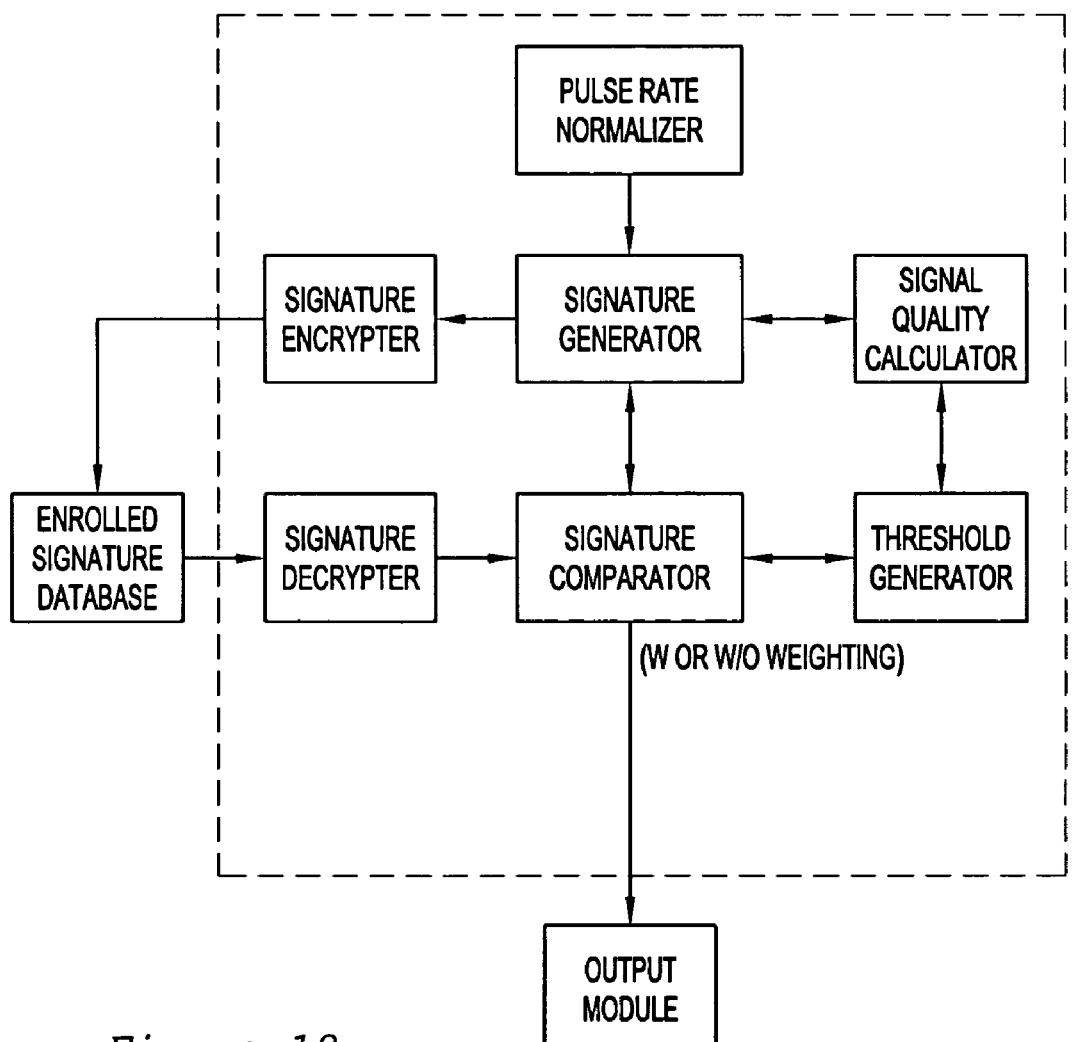
FIG. 18 shows a functional component diagram of a preferred signal processor.

Preferred Embodiment that may be Used with All Aspects:

FIG. 17 shows a functional diagram of a preferred system. Likewise, FIG. 18 shows a functional diagram of a preferred signal processor. The term "processor" is used herein generically and the processing may be done by physically discrete components, such as with co-processors on an IC chip, or the processor may comprise a physically integral unit.

General Example That May Be Used With All Aspects:

ENROLLMENT ALGORITHM

The following is an example algorithm for an enrollment phase that may be used with any of the foregoing aspects:

i. Let $x_i(n)$ represent a 20-second, 250 Hz digitized sample of the $i^{th}$ new subject, where n denotes discrete units of time.
ii. $x_i(n)$ is band-pass filtered in the range 4 Hz-40 Hz.
iii. The filtered signal is denoted $y_i(n)$.
iv. The filtered signal $y_i(n)$ is searched for QRS complexes, identifying the 'R' peaks as anchor points.
v. The filtered signal $y_i(n)$ is maintained or inverted to obtain positive 'R' peaks.
vi. The identified QRS complexes are counted to establish an average pulse rate reading $PR_i$.
vii. The filtered signal $y_i(n)$ is segmented around the anchor points, taking 50 samples before and 90 samples after each 'R' anchor point.
viii. Each data segment is normalized by the amplitude of the 'R' anchor point.
ix. The segments are aligned around the anchor points and averaged to produce the subject electro-cardiologic signal, denoted $s_i(n)$.
x. The subject electro-cardiologic signal $s_i(n)$ is adjusted according to the average pulse rate $PR_i$, by normalizing 'P' and 'T' latencies according to the pulse rate. The adjusted electro-cardiologic signal is denoted $v_i(n)$.
xi. The pulse rate adjusted subject's electro-cardiologic signal $v_i(n)$ is added to the database and is introduced into a grand-average $T(n)$
xii. A set of electro-biometric signatures $\Phi_i$ is constructed by subtraction of the grand-average $T(n)$ from each of the pulse rate adjusted electro-cardiologic signals stored in the system database.

EXAMPLE: RECOGNITION ALGORITHM

The following is an example an algorithm for the recognition phase:

i. Let $x_j(n)$ represent a 10-second, 250 Hz digitized sample of the tested subject.
ii. $x_j(n)$ is band-pass filtered in the range 4 Hz-40 Hz.
iii. The filtered signal is denoted $y_j(n)$.
iv. The filtered signal $y_j(n)$ is searched for the locations of QRS complexes, using the R peak as an anchor point.
v. The filtered signal $y_j(n)$ is maintained or inverted to obtain positive 'R' peaks.
vi. The identified QRS complexes are counted to establish ant average pulse rate reading $PR_i$.
vii. The filtered signal $y_j(n)$ is segmented around the anchor points, taking 50 samples before and 90 samples after each anchor point.
viii. The segments are aligned around the anchor points and averaged to produce the subject electro-cardiologic signal, denoted $s_j(n)$.
ix. The subject electro-cardiologic signal $s_j(n)$ is normalized according to the average pulse rate $PR_j$. The pulse rate adjusted subject electro-cardiologic signal is denoted $v_j(n)$.
x. An electro-biometric signature $\sigma_j$ is constructed by subtraction of the grand-average $T(n)$ from the pulse rate adjusted electro-cardiologic signal $v_j(n)$.
xi. The correlation coefficients between the electro-biometric signature $\sigma_j$ and all the enrolled electro-biometric signatures $\Phi_i$ are calculated and squared, maintaining their original arithmetic sign.
xii. The largest sign-maintained squared correlation value is selected and compared to a preset threshold.
xiii. If the selected largest sign maintained squared correlation value is larger than the preset threshold then a positive match is indicated, and the subject is identified.

Thus, a method and apparatus of acquisition, processing, and analysis of electro-cardiologic signals for electro-biometric identity recognition may include any subset of the following enrollment and recognition steps:

Enrollment
Acquisition, digitization, and storage of electro-cardiologic signals from subjects;
a. Formation of an electro-cardiologic signal database;
b. Partition of the template database into several subsets based on electro-cardiologic signal similarity;
c. Construction of one or more grand averages;
d. Derivation of subject-specific electro-biometric signatures.

Recognition
Verification
The newly captured electro-biometric signature is compared with the subject specific enrolled electro-biometric signature template;
e. Correlation and confidence analysis of the newly captured subject electro-biometric signature with the relevant stored electro-biometric signature template;

f. Display and registration of the recognition result and/or activation of a physical or virtual local/remote mechanism.

Identification

The newly captured electro-biometric signature is compared with all of the electro-biometric signature templates participating in the database;

g. Correlation and confidence analysis of the newly captured subject electro-biometric signature with all stored electro-biometric signature templates;

h. Display and registration of the recognition result and/or activation of a physical or virtual local/remote mechanism.

Others may readily modify and/or adapt the embodiments herein for various applications without undue experimentation and without departing from the generic concept. Such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms and still fall within the literal or equivalent scope of the claims.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A method for identifying an individual, comprising:
producing and storing a first biometric signature that identifies a specific individual by forming the difference between a representation of a heartbeat pattern of the specific individual and a stored representation of common features of heartbeat patterns of a plurality of individuals;
after said producing step, obtaining a representation of a heartbeat pattern of a selected individual and producing a second biometric signature by forming the difference between the heartbeat pattern of the selected individual and the stored representation of the common features of the heartbeat patterns of the plurality of individuals; and
comparing said second biometric signature with said first biometric signature to determine whether the selected individual is the specific individual.

2. The method of claim 1 wherein:
said step of producing and storing comprises producing and storing a plurality of first biometric signatures, each identifying a respective individual, by forming the difference between a representation of the heartbeat pattern of each respective individual and the stored representation of the common features of the heartbeat patterns; and
said step of comparing is carried out with respect to each of said first biometric signatures.

3. The method of claim 2 comprising a preliminary step of obtaining representations of the heartbeat patterns of a plurality of individuals, and deriving and storing the representation of the common features of the heartbeat patterns of a plurality of individuals from at least a selected number of the representations.

4. The method of claim 3 wherein said step of deriving and storing the representation of the common features of the heartbeat patterns of a plurality of individuals comprises deriving and storing a plurality of representations of the common features of the heartbeat patterns each from a respectively different group of the plurality of individuals.

5. The method of claim 3, wherein said step of deriving and storing the representation of the common features of the heartbeat patterns of a plurality of individuals comprises producing an average of the heartbeat patterns of the plurality of individuals.

6. The method of claim 3, wherein said step of deriving and storing the representation of the common features of the heartbeat patterns of a plurality of individuals comprises performing one of principal component analysis or wavelet decomposition.

7. The method of claim 2 wherein said step of comparing comprises correlating said second biometric signature with each of said first biometric signatures and identifying that one of said first biometric signatures that correlates most closely to said second biometric signature.

8. The method of claim 7, wherein said step of correlating comprises obtaining a correlation coefficient associated with each first biometric signature, and said step of comparing further comprises comparing the correlation coefficient associated with the identified first biometric signature with a correlation coefficient threshold.

9. The method of claim 7 further comprising the steps of:
a) transforming one or more of said correlations; and
b) generating a dynamic threshold for said correlation.

10. The method of biometric identification system of claim 9 wherein the step of transforming one ore more said correlations is used to generate a Z-score.

11. The method of biometric identification of claim 9 wherein said step of transforming said one or more correlations squares said one or more correlations.

12. The method of claim 2 further comprising the steps of:
a) comparing the result of said comparison with an identification threshold; and
b) affecting a locking mechanism based on said comparison.

13. The method of claim 2 further comprising the steps of:
a) comparing the result of said comparison with an identification threshold; and
b) permitting or denying room access based upon said comparison.

14. The method of claim 1 wherein said step of comparing comprises: correlating said second biometric signature with said first biometric signature to obtain a correlation coefficient; and comparing the correlation coefficient associated with the first biometric signature with a correlation coefficient threshold.

15. The method of biometric identification of claim 14 further comprising the step of outputting a result of said comparison.

16. The method of claim 1 wherein said step producing and storing a first biometric signature comprises storing the signature in a local database.

17. The method of claim 1 wherein said step producing and storing a first biometric signature comprises storing the signature in a remote database.

18. The method of claim 1 wherein said step of obtaining a representation of the heartbeat pattern of a selected individual comprises compensating for deviations in a pulse rate of the selected individual.

19. The method of claim 1 wherein said step of obtaining a representation of the heartbeat pattern of a selected individual comprises obtaining several representations of heartbeat patterns.

20. The method of claim 1 wherein said step of producing and storing a first biometric signature of a specific individual comprises obtaining a plurality of representations of the heartbeat pattern of the specific individual over a period of time and producing successive first biometric signatures each from a respective one of the plurality of representations of the heartbeat pattern of the specific individual.

21. The method for identifying an individual of claim 1 wherein said stored representation is an analytical representation of common features of heartbeat patterns.

22. The method of claim 1 further comprising the steps of:
a) processing a first ECG signal as part of said step of producing and storing said first biometric signature, an ECG signature template, that is compared with said second biometric signature; and
b) outputting the result of said comparison.

23. The method of claim 22 wherein said processing step removes common features of one or more ECG components from the ECG signal by subtracting common features of one or more ECG components provided by an analytical ECG model.

24. The method of claim 22 further comprising the steps of g) creating a database of such ECG signature templates, h) dividing the ECG signature templates into subsets, and i) using at least one database subset to remove common features of one or more ECG components from an ECG signal.

25. The method of biometric identification of claim 22 further comprising the steps of:
a) correlating said second biometric signature with at least one ECG signature template from a signal taken at a normalized pulse rate or normalized for pulse rate; and
b) comparing the result of said correlation with a threshold.

26. The method of biometric identification system of claim 25 wherein said processing step processes said signal digitally.

27. The method of biometric identification of claim 25 further comprising the step of obtaining a non-ECG biometric reading.

28. The method of biometric identification system of claim 27 further comprising the step of evaluating said non-ECG biometric reading and said outputted comparison result to identify an individual.

29. The method of claim 22 further comprising a step of controlling access to an Internet Website based on the result of said comparison step.

30. The method of claim 29 wherein said comparison step compares said second biometric signature with more than one ECG signature template.

31. The method of claim 29 wherein said comparison step compares the width of a QRS signal complex with the width of one or more reference signal QRS complexes.

32. The method of claim 1 further comprising the step of calculating the quality of a signal used to obtain a representation of a heartbeat pattern.

33. The method of biometric identification system of claim 32 wherein said step of calculating signal quality calculates a Q-value.

34. The method of biometric identification system of claim 32 further comprising the step of adjusting a time of signal acquisition based on the quality of the signal.

35. The method of biometric identification system of claim 32 further comprising the step of acquiring a new signal in response to the signal quality calculation.

36. The method of claim 1 further comprising the steps of:
a) encrypting at least said first signature; and
b) adding said encrypted signature to an enrolled signature database.

37. The method of biometric identification system of claim 36 wherein said signature encryption step scrambles the signature using a public key infrastructure technique.

38. The method of claim 1 further comprising the steps of:
a) acquiring an ECG signal using ultra-high input impedance probes; and
b) processing said ECG signal to generate a biometric signature.

39. The biometric identification system of claim 38 wherein said ultra-high input resistance probes have ultra-low noise characteristics.

40. The method of biometric identification of claim 1 further comprising the step of obtaining a non-ECG biometric reading.

41. The method for identifying an individual of claim 1 further comprising the step of obtaining additional heartbeat patterns and adding them to an individual's data file when changes in data signals are encountered.

42. The method of claim 41 further comprising the step of processing newly acquired heartbeat patterns to form an enrolled biometric signature.

43. The method for identifying an individual of claim 1 wherein an enrolled biometric signature database is automatically adjusted to reflect changes in heartbeat pattern over long-term operation.

44. Apparatus for identifying an individual, comprising:
means for producing and storing a first biometric signature that identifies a specific individual by forming the difference between a representation of a heartbeat pattern of the specific individual and a stored representation of common features of the heartbeat patterns of a plurality of individuals;
means for obtaining, after the first biometric signature has been produced and stored, a representation of the heartbeat pattern of a selected individual and producing a second biometric signature by forming the difference between the heartbeat pattern of the selected individual and the stored representation of the common features average of the heartbeat patterns of the plurality of individuals; and
means for comparing said second biometric signature with said first biometric signature to determine whether the selected individual is the specific individual.

45. Apparatus for identifying an individual, comprising:
means for producing and storing a first biometric signature that identifies a specific individual by forming the difference between a representation of a heartbeat pattern of the specific individual and a stored representation of common features of the heartbeat patterns of a plurality of individuals;
means for obtaining, after the first biometric signature has been produced and stored, a representation of the heartbeat pattern of a selected individual and producing a second biometric signature by forming the difference between the heartbeat pattern of the selected individual and the stored representation of a common features average of the heartbeat patterns of a plurality of individuals;

means for comparing said second biometric signature with said first biometric signature to determine whether the selected individual is the specific individual; and a non-ECG biometric acquisition module.

46. Apparatus for identifying an individual, comprising:

means for producing and storing a first biometric signature that identifies a specific individual by forming the difference between a representation of a heartbeat pattern of the specific individual and a stored representation of common features of the heartbeat patterns of a plurality of individuals;

means for obtaining, after the first biometric signature has been produced and stored, a representation of the heartbeat pattern of a selected individual and producing a second biometric signature by forming the difference between the heartbeat pattern of the selected individual and the stored representation of a common features average of the heartbeat patterns of a plurality of individuals;

means for comparing said second biometric signature with said first biometric signature to determine whether the selected individual is the specific individual; and means for obtaining additional heartbeat patterns and adding them to an individual's data file when changes in data signals are encountered.

47. The apparatus for identifying an individual of claim 46 further comprising means for processing newly acquired heartbeat patterns to form an enrolled biometric signature.

48. Apparatus for identifying an individual, comprising:

means for producing and storing a first biometric signature that identifies a specific individual by forming the difference between a representation of a heartbeat pattern of the specific individual and a stored representation of common features of the heartbeat patterns of a plurality of individuals;

means for obtaining, after the first biometric signature has been produced and stored, a representation of the heartbeat pattern of a selected individual and producing a second biometric signature by forming the difference between the heartbeat pattern of the selected individual and the stored representation of the common features average of the heartbeat patterns of the plurality of individuals;

means for comparing said second biometric signature with said first biometric signature to determine whether the selected individual is the specific individual; and means for automatically adjusting an enrolled biometric signature database to reflect changes in heartbeat pattern over long-term operation.

* * * * *